(12) United States Patent
Nelson et al.

(10) Patent No.: US 7,959,908 B2
(45) Date of Patent: Jun. 14, 2011

(54) METHODS OF TREATING VIRAL INFECTIONS USING IL-21

(75) Inventors: Andrew J. Nelson, Shoreline, WA (US); Wayne Kindsvogel, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/355,650

(22) Filed: Jan. 16, 2009

(65) Prior Publication Data

US 2009/0202477 A1 Aug. 13, 2009

Related U.S. Application Data

(63) Continuation of application No. 11/553,367, filed on Oct. 26, 2006, now abandoned, which is a continuation of application No. 10/456,262, filed on Jun. 6, 2003, now abandoned.

(60) Provisional application No. 60/387,127, filed on Jun. 7, 2002.

(51) Int. Cl.
*A61K 38/20* (2006.01)
(52) U.S. Cl. ........ 424/85.2; 530/351; 435/69.7; 435/7.2
(58) Field of Classification Search .................. None
See application file for complete search history.

(56) References Cited

U.S. PATENT DOCUMENTS

| | | | | |
|---|---|---|---|---|
| 6,057,128 | A | 5/2000 | Donaldson et al. | 435/69.1 |
| 6,307,024 | B1 | 10/2001 | Novak et al. | |
| 6,605,272 | B2 | 8/2003 | Novak et al. | 424/85.2 |
| 6,686,178 | B2 | 2/2004 | Novak et al. | 435/69.52 |
| 2004/0016010 | A1 | 1/2004 | Kasaian et al. | |

FOREIGN PATENT DOCUMENTS

| | | |
|---|---|---|
| WO | 03/028630 | 4/2003 |
| WO | 03/082212 | 10/2003 |
| WO | 03/087320 | 10/2003 |
| WO | 2004/007682 | 1/2004 |

OTHER PUBLICATIONS

U.S. Appl. No. 10/456,780, filed Jun. 6, 2003, Nelson et al.
U.S. Appl. No. 10/735,149, filed Dec. 12, 2003, Zamost et al.
U.S. Appl. No. 11/539,036, filed Oct. 5, 2006, Zamost et al.
U.S. Appl. No. 11/539,045, filed Oct. 5, 2006, Zamost et al.
U.S. Appl. No. 11/539,055, filed Oct. 5, 2006, Zamost et al.
U.S. Appl. No. 11/134,489, filed May 20, 2005, Kingsvogel et al.
U.S. Appl. No. 11/553,367, filed Oct. 26, 2006, Nelson et al.
U.S. Appl. No. 11/553,381, filed Oct. 26, 2006, Nelson et al.
U.S. Appl. No. 11/553,389, filed Oct. 26, 2006, Nelson et al.
U.S. Appl. No. 11/553,392, filed Oct. 26, 2006, Nelson et al.
U.S. Appl. No. 11/553,395, filed Oct. 26, 2006, Nelson et al.
U.S. Appl. No. 11/548,196, filed Oct. 10, 2006, Nelson et al.
U.S. Appl. No. 11/548,202, filed Oct. 10, 2006, Nelson et al.
U.S. Appl. No. 11/548,517, filed Oct. 11, 2006, Nelson et al.
U.S. Appl. No. 11/548,530, filed Oct. 11, 2006, Nelson et al.
U.S. Appl. No. 11/548,538, filed Oct. 11, 2006, Nelson et al.
U.S. Appl. No. 11/548,554, filed Oct. 11, 2006, Nelson et al.
U.S. Appl. No. 11/548,567, filed Oct. 11, 2006, Nelson et al.
U.S. Appl. No. 11/548,574, filed Oct. 11, 2006, Nelson et al.
U.S. Appl. No. 11/548,585, filed Oct. 11, 2006, Nelson et al.
U.S. Appl. No. 11/548,877, filed Oct. 12, 2006, Nelson et al.
U.S. Appl. No. 11/548,946, filed Oct. 12, 2006, Nelson et al.
U.S. Appl. No. 11/548,963, filed Oct. 12, 2006, Nelson et al.
U.S. Appl. No. 11/548,969, filed Oct. 12, 2006, Nelson et al.
U.S. Appl. No. 11/539,479, filed Oct. 6, 2006, Kindsvogel et al.
U.S. Appl. No. 11/539,493, filed Oct. 6, 2006, Kindsvogel et al.
U.S. Appl. No. 11/539,511, filed Oct. 6, 2006, Kindsvogel et al.
U.S. Appl. No. 11/285,970, filed Nov. 23, 2005, Yee.
U.S. Appl. No. 10/659,684, filed Sep. 10, 2003, Novak et al.
U.S. Appl. No. 11/549,772, filed Oct. 16, 2006, Novak et al.
U.S. Appl. No. 11/551,807, filed Oct. 23, 2006, Novak et al.
U.S. Appl. No. 11/551,344, filed Oct. 20, 2006, Novak et al.
U.S. Appl. No. 11/549,868, filed Oct. 16, 2006, Novak et al.
U.S. Appl. No. 11/551,356, filed Oct. 20, 2006, Novak et al.
U.S. Appl. No. 11/551,362, filed Oct. 20, 2006, Novak et al.
U.S. Appl. No. 11/551,368, filed Oct. 20, 2006, Novak et al.
U.S. Appl. No. 11/551,811, filed Oct. 23, 2006, Novak et al.
U.S. Appl. No. 11/551,820, filed Oct. 23, 2006, Novak et al.
U.S. Appl. No. 10/787,442, filed Feb. 26, 2004, Novak et al.
U.S. Appl. No. 11/532,776, filed Sep. 18, 2006, Novak et al.
U.S. Appl. No. 11/551,127, filed Oct. 19, 2006, Novak et al.
U.S. Appl. No. 11/551,136, filed Oct. 19, 2006, Novak et al.
U.S. Appl. No. 11/551,139, filed Oct. 19, 2006, Novak et al.
U.S. Appl. No. 11/551,144, filed Oct. 19, 2006, Novak et al.
U.S. Appl. No. 11/551,349, filed Oct. 20, 2006, Novak et al.
U.S. Appl. No. 11/563,928, filed Nov. 28, 2006, Sivakumar et al.
U.S. Appl. No. 11/564,001, filed Nov. 28, 2006, Sivakumar et al.
U.S. Appl. No. 11/346,580, filed Feb. 2, 2006, Novak et al.
Brandt et al., "Interleukin-21 inhibits dendritic cell activation and maturation," *Blood* 102(12):4090-8, 2003.
Cui et al., "Cytokine genetic adjuvant facilitates prophylactic intravascular DNA vaccine against acute and latent herpes simplex virus infection in mice," *Gene Therapy* 12:160-168, 2005.
Strengell et al., "IL-21 Up-Regulates the Expression of Genes Associated with Innate Immunity and Th1 Response" J. Immunol. 3601-3605, 2002.
Eberl, "Differentiation of human γδ T cells towards distinct memory phenotypes," *Cellular Immunology* 218:1-6, 2002.
Eberl, "Accumulation of a potent γδ T-cell stimulator after deletion of the *lytB* gene in *Escherichia coli*," *Immunology* 106:200-211, 2002.
Witek, "Primary Macrophages Express IL-21R and Resond to IL-21 by Proliferating and Secreting Increased Levels of Cytokines and Chemokines," P-2-12, 2002. Publisher Not Available.
1483966, Marra, WashU-HHMI Mouse EST Project, 1996.
Parrish-Novak et al., "Interleukin 21 and its receptor are involved in NK cell expansion and regulation of lymphocyte function," *Nature* 408:57-63, 2000.
Van Leeuwen et al., "Proliferation Requirements of Cytomegalovirus-Specific, Effector-Type Human CD8+ T Cells," *J. Immunol.* 5838-5843, 2002.
Fahey et al., "Status of immune-based therapy in HIV infection and AIDS," *Clin. Exp. Immunol.* 88:1-5, 1992.

*Primary Examiner* — Dong Jiang
(74) *Attorney, Agent, or Firm* — Michelle L. Lewis

(57) ABSTRACT

Methods for treating mammals with infections, particularly viral infections using molecules that have an IL-21 functional activity are described. The molecules having IL-21 functional activities include polypeptides that have homology to the human IL-21 polypeptide sequence and proteins fused to a polypeptide with IL-21 functional activity. The molecules can be used as a monotherapy or in combination with other known antimicrobial or antiviral therapeutics.

6 Claims, No Drawings

SEQUENCE LISTING

```
<160> NUMBER OF SEQ ID NOS: 17

<210> SEQ ID NO 1
<211> LENGTH: 642
<212> TYPE: DNA
<213> ORGANISM: Homo sapiens
<220> FEATURE:
<221> NAME/KEY: CDS
<222> LOCATION: (47)...(532)

<400> SEQUENCE: 1
gctgaagtga aaacgagacc aaggtctagc tctactgttg gtactt atg aga tcc         55
                                                Met Arg Ser
                                                 1 agt cct ggc aac atg gag agg att gtc atc tgt ctg atg gtc atc ttc       103
Ser Pro Gly Asn Met Glu Arg Ile Val Ile Cys Leu Met Val Ile Phe
  5                  10                  15 ttg ggg aca ctg gtc cac aaa tca agc tcc caa ggt caa gat cgc cac       151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat       199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta       247
Tyr Val Asn Asp Leu Val Pro Glu Phe Leu Pro Ala Pro Glu Asp Val
             55                  60                  65 gag aca aac tgt gag tgg tca gct ttt tcc tgt ttt cag aag gcc caa       295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca       343
Leu Lys Ser Ala Asn Thr Gly Asn Asn Glu Arg Ile Ile Asn Val Ser
     85                  90                  95 att aaa aag ctg aag agg aaa cca cct tcc aca aat gca ggg aga aga       391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa       439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg       487
Pro Pro Lys Glu Phe Leu Glu Arg Phe Lys Ser Leu Leu Gln Lys Met
            135                 140                 145 att cat cag cat ctg tcc tct aga aca cac gga agt gaa gat tcc            532
Ile His Gln His Leu Ser Ser Arg Thr His Gly Ser Glu Asp Ser
        150                 155                 160 tgaggatcta acttgcagtt ggacactatg ttacatactc taatatagta gtgaaagtca     592
tttctttgta ttccaagtgg aggagcccta ttaaattata taagaaata                 642

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
```

-continued

```
               1               5                  10                 15
            Val Ile Phe Leu Gly Thr Leu Val His Lys Ser Ser Gln Gly Gln
                           20                 25                 30

Asp Arg His Met Ile Arg Met Arg Gln Leu Ile Asp Ile Val Asp Gln
                           35                 40                 45

Leu Lys Asn Tyr Val Asn Asp Leu Val Pro Glu Phe Leu Pro Ala Pro
             50                 55                 60

Glu Asp Val Glu Thr Asn Cys Glu Trp Ser Ala Phe Ser Cys Phe Gln
             65                 70                 75                 80

Lys Ala Gln Leu Lys Ser Ala Asn Thr Gly Asn Asn Glu Arg Ile Ile
                               85                 90                 95

Asn Val Ser Ile Lys Lys Leu Lys Arg Lys Pro Pro Ser Thr Asn Ala
                              100                105                110

Gly Arg Arg Gln Lys His Arg Leu Thr Cys Pro Ser Cys Asp Ser Tyr
                              115                120                125

Glu Lys Lys Pro Pro Lys Glu Phe Leu Glu Arg Phe Lys Ser Leu Leu
                              130                135                140

Gln Lys Met Ile His Gln His Leu Ser Ser Arg Thr His Gly Ser Glu
            145                150                155                160

Asp Ser

<210> SEQ ID NO 3
<211> LENGTH: 3072
<212> TYPE: DNA
<213> ORGANISM: Mus musculus
<220> FEATURE:
<221> NAME/KEY: CDS
<222> LOCATION: (54)...(491)

<400> SEQUENCE: 3
gagaaccaga ccaaggccct gtcatcagct cctggagact cagttctggt ggc atg          56
                                                           Met
                                                            1 gag agg acc ctt gtc tgt ctg gta gtc atc ttc ttg ggg aca gtg gcc        104
Glu Arg Thr Leu Val Cys Leu Val Val Ile Phe Leu Gly Thr Val Ala
            5                  10                  15 cat aaa tca agc ccc caa ggg cca gat cgc ctc ctg att aga ctt cgt        152
His Lys Ser Ser Pro Gln Gly Pro Asp Arg Leu Leu Ile Arg Leu Arg
         20                  25                  30 cac ctt att gac att gtt gaa cag ctg aaa atc tat gaa aat gac ttg        200
His Leu Ile Asp Ile Val Glu Gln Leu Lys Ile Tyr Glu Asn Asp Leu
     35                  40                  45 gat cct gaa ctt cta tca gct cca caa gat gta aag ggg cac tgt gag        248
Asp Pro Glu Leu Leu Ser Ala Pro Gln Asp Val Lys Gly His Cys Glu
 50                  55                  60                  65 cat gca gct ttt gcc tgt ttt cag aag gcc aaa ctc aag cca tca aac        296
His Ala Ala Phe Ala Cys Phe Gln Lys Ala Lys Leu Lys Pro Ser Asn
                 70                  75                  80 cct gga aac aat aag aca ttc atc att gac ctc gtg gcc cag ctc agg        344
Pro Gly Asn Asn Lys Thr Phe Ile Ile Asp Leu Val Ala Gln Leu Arg
             85                  90                  95 agg agg ctg cct gcc agg agg gga gga aag aaa cag aag cac ata gct        392
Arg Arg Leu Pro Ala Arg Arg Gly Gly Lys Lys Gln Lys His Ile Ala
        100                 105                 110 aaa tgc cct tcc tgt gat tcg tat gag aaa agg aca ccc aaa gaa ttc        440
Lys Cys Pro Ser Cys Asp Ser Tyr Glu Lys Arg Thr Pro Lys Glu Phe
    115                 120                 125 cta gaa aga cta aaa tgg ctc ctt caa aag atg att cat cag cat ctc        488
Leu Glu Arg Leu Lys Trp Leu Leu Gln Lys Met Ile His Gln His Leu
130                 135                 140
```

```
                130         135         140         145
tcc tagaacacat aggacccgaa gattcctgag gatccgagaa gattcccgag          541
Ser gactgaggag acgccggaca ctatagacgc tcacgaatgc aggagtacat cttgcctctt    601
gggattgcaa gtggagaagt acgatacgtt atgataagaa caactcagaa aagctatagg    661
ttaagatcct ttcgcccatt aactaagcag acattgtggt tccctgcaca gactccatgc    721
tgtcaacatg gaaaatctca actcaacaag agcccagctt cccgtgtcag ggatttctgg    781
tgcttctcaa gctgtggctt catcttattg cccaactgtg acattctttg attggaaggg    841
gaaaactaaa gcttttagca aaaatacagc tagggaattt gtcgatctgc gagagtaaga    901
cctcttatga tcctaacgga atgatgtaag ctggaaataa taagcataag atgaaattga    961
aaattgaagt ctttattctt taagaaaaac tttgtacttg aaagcatgtc tgaagagttt   1021
actcattacc acaaacatct agcatattga taactaacat ctttatactc tacaagagag   1081
gctttccaga taggtacagt ttttcttctc tattaggtct atcaaaattt aacctattat   1141
gagggtcacc cctggctttc actgtttttc taaagaggca agggtgtagt aagaagcagg   1201
cttaagttgc cttcctccca atgtcaagtt cctttataag ctaatagttt aatcttgtga   1261
agatggcaat gaaagcctgt ggaagtgcaa acctcactat cttctggagc caagtagaat   1321
tttcaagttt gtagctctca cctcaagtgg ttatgggtgt cctgtgatga atctgctagc   1381
tccagcctca gtctcctctc ccacatcctt tcctttcttt cctctttgaa acttctaaga   1441
aaaagcaatc caaacaagtt cagcacttaa gacacattgc atgcacactt ttgataagtt   1501
aaatccaacc atctatttaa aatcaaaatc aggagatgag ccaagagacc agaggttctg   1561
ttccagtttt aaacagactt ttactgaaca tcccaatctt ttaaccacag aggctaaatt   1621
gagcaaatag ttttgccatt tgatataatt tccaacagta tgtttcaatg tcaagttaaa   1681
aagtctacaa agctattttc cctggagtgg tatcatcgct ttgagaattt cttatggtta   1741
aaatggatct gagatccaag catggcctgg gggatggttt tgatctaagg aaaaaggtgt   1801
ctgtacctca cagtgccttt aaaacaagca gagatcccgt gtaccgccct aagatagcac   1861
agactagtgt taactgattc ccagaaaagt gtcacaatca gaaccaacgc attctcttaa   1921
actttaaaaa tatgtattgc aaagaacttg tgtaactgta aatgtgtgac tgttgatgac   1981
attatacaca catagcccac gtaagtgtcc aatggtgcta gcattggttg ctgagtttgc   2041
tgctcgaaag ctgaagcaga gatgcagtcc ttcacaaagc aatgatggac agagagggga   2101
gtctccatgt tttattcttt tgttgtttct ggctgtgtaa ctgttgactt cttgacattg   2161
tgatttttat atttaagaca atgtatttat tttggtgtgt ttattgttct agccttttaa   2221
atcactgaca atttctaatc aagaagtaca aataattcaa tgcagcacag gctaagagct   2281
tgtatcgttt ggaaaagcca gtgaaggctt ctccactagc catgggaaag ctacgcttta   2341
gagtaaacta gacaaaattg cacagcagtc ttgaacctct ctgtgctcaa gactcagcca   2401
gtcctttgac attattgttc actgtgggtg ggaacacatt ggacctgaca cactgttgtg   2461
tgtccatgaa ggttgccact ggtgtaagct ttttttggtt ttcattctct tatctgtaga   2521
acaagaatgt ggggcttcc taagtcattt ctgtattttta ttctgaactt cgtatgtctg   2581
agttttaatg ttttgagtac tcttacagga acacctgacc acacttttga gttaaatttt   2641
atcccaagtg tgatatttag ttgttcaaaa agggaaggga tatacataca tacatacata   2701
catacataca tatatatata tatatataca tatatatata tatatatatg tatatatata   2761
tatatataga gagagagaga gagagagaga gagaaagaga gagaggttgt tgtaggtcat   2821
```

```
aggagttcag aggaaatcag ttatggccgt taatactgta gctgaaagtg ttttctttgt    2881
gaataaattc atagcattat tgatctatgt tattgctctg ttttatttac agtcacacct    2941
gagaatttag ttttaatatg aatgatgtac tttataactt aatgattatt tattatgtat    3001
ttggttttga atgtttgtgt tcatggcttc ttatttaaga cctgatcata ttaaatgcta    3061
cccagtccgg a                                                        3072

<210> SEQ ID NO 4
<211> LENGTH: 146
<212> TYPE: PRT
<213> ORGANISM: Mus musculus

<400> SEQUENCE: 4

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145

<210> SEQ ID NO 5
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 5 atg ccg cgt ggc tgg gcc gcc ccc ttg ctc ctg ctg ctc cag gga          48
Met Pro Arg Gly Trp Ala Ala Pro Leu Leu Leu Leu Leu Gln Gly
1               5                   10                  15 ggc tgg ggc tgc ccc gac ctc gtc tgc tac acc gat tac ctc cag acg     96
Gly Trp Gly Cys Pro Asp Leu Val Cys Tyr Thr Asp Tyr Leu Gln Thr
            20                  25                  30 gtc atc tgc atc ctg gaa atg tgg aac ctc cac ccc agc acg ctc acc    144
Val Ile Cys Ile Leu Glu Met Trp Asn Leu His Pro Ser Thr Leu Thr
        35                  40                  45 ctt acc tgg caa gac cag tat gaa gag ctg aag gac gag gcc acc tcc    192
Leu Thr Trp Gln Asp Gln Tyr Glu Glu Leu Lys Asp Glu Ala Thr Ser
    50                  55                  60 tgc agc ctc cac agg tcg gcc cac aat gcc acg cat gcc acc tac acc    240
Cys Ser Leu His Arg Ser Ala His Asn Ala Thr His Ala Thr Tyr Thr
65                  70                  75                  80
```

```
tgc cac atg gat gta ttc cac ttc atg gcc gac gac att ttc agt gtc     288
Cys His Met Asp Val Phe His Phe Met Ala Asp Asp Ile Phe Ser Val
                85                  90                  95 aac atc aca gac cag tct ggc aac tac tcc cag gag tgt ggc agc ttt     336
Asn Ile Thr Asp Gln Ser Gly Asn Tyr Ser Gln Glu Cys Gly Ser Phe
            100                 105                 110 ctc ctg gct gag agc atc aag ccg gct ccc cct ttc aac gtg act gtg     384
Leu Leu Ala Glu Ser Ile Lys Pro Ala Pro Pro Phe Asn Val Thr Val
        115                 120                 125 acc ttc tca gga cag tat aat atc tcc tgg cgc tca gat tac gaa gac     432
Thr Phe Ser Gly Gln Tyr Asn Ile Ser Trp Arg Ser Asp Tyr Glu Asp
    130                 135                 140 cct gcc ttc tac atg ctg aag ggc aag ctt cag tat gag ctg cag tac     480
Pro Ala Phe Tyr Met Leu Lys Gly Lys Leu Gln Tyr Glu Leu Gln Tyr
145                 150                 155                 160 agg aac cgg gga gac ccc tgg gct gtg agt ccg agg aga aag ctg atc     528
Arg Asn Arg Gly Asp Pro Trp Ala Val Ser Pro Arg Arg Lys Leu Ile
                165                 170                 175 tca gtg gac tca aga agt gtc tcc ctc ctc ccc ctg gag ttc cgc aaa     576
Ser Val Asp Ser Arg Ser Val Ser Leu Leu Pro Leu Glu Phe Arg Lys
            180                 185                 190 gac tcg agc tat gag ctg cag gtg cgg gca ggg ccc atg cct ggc tcc     624
Asp Ser Ser Tyr Glu Leu Gln Val Arg Ala Gly Pro Met Pro Gly Ser
        195                 200                 205 tcc tac cag ggg acc tgg agt gaa tgg agt gac ccg gtc atc ttt cag     672
Ser Tyr Gln Gly Thr Trp Ser Glu Trp Ser Asp Pro Val Ile Phe Gln
    210                 215                 220 acc cag tca gag gag tta aag gaa ggc tgg aac cct cac ctg ctg ctt     720
Thr Gln Ser Glu Glu Leu Lys Glu Gly Trp Asn Pro His Leu Leu Leu
225                 230                 235                 240 ctc ctc ctg ctt gtc ata gtc ttc att cct gcc ttc tgg agc ctg aag     768
Leu Leu Leu Leu Val Ile Val Phe Ile Pro Ala Phe Trp Ser Leu Lys
                245                 250                 255 acc cat cca ttg tgg agg cta tgg aag aag ata tgg gcc gtc ccc agc     816
Thr His Pro Leu Trp Arg Leu Trp Lys Lys Ile Trp Ala Val Pro Ser
            260                 265                 270 cct gag cgg ttc ttc atg ccc ctg tac aag ggc tgc agc gga gac ttc     864
Pro Glu Arg Phe Phe Met Pro Leu Tyr Lys Gly Cys Ser Gly Asp Phe
        275                 280                 285 aag aaa tgg gtg ggt gca ccc ttc act ggc tcc agc ctg gag ctg gga     912
Lys Lys Trp Val Gly Ala Pro Phe Thr Gly Ser Ser Leu Glu Leu Gly
    290                 295                 300 ccc tgg agc cca gag gtg ccc tcc acc ctg gag gtg tac agc tgc cac     960
Pro Trp Ser Pro Glu Val Pro Ser Thr Leu Glu Val Tyr Ser Cys His
305                 310                 315                 320 cca cca cgg agc ccg gcc aag agg ctg cag ctc acg gag cta caa gaa    1008
Pro Pro Arg Ser Pro Ala Lys Arg Leu Gln Leu Thr Glu Leu Gln Glu
                325                 330                 335 cca gca gag ctg gtg gag tct gac ggt gtg ccc aag ccc agc ttc tgg    1056
Pro Ala Glu Leu Val Glu Ser Asp Gly Val Pro Lys Pro Ser Phe Trp
            340                 345                 350 ccg aca gcc cag aac tcg ggg gca tca gct tac agt gag gag agg gat    1104
Pro Thr Ala Gln Asn Ser Gly Gly Ser Ala Tyr Ser Glu Glu Arg Asp
        355                 360                 365 cgg cca tac ggc ctg gtg tcc att gac aca gtg act gtg cta gat gca    1152
Arg Pro Tyr Gly Leu Val Ser Ile Asp Thr Val Thr Val Leu Asp Ala
    370                 375                 380 gag ggg cca tgc acc tgg ccc tgc agc tgt gag gat gac ggc tac cca    1200
Glu Gly Pro Cys Thr Trp Pro Cys Ser Cys Glu Asp Asp Gly Tyr Pro
385                 390                 395                 400
```

-continued

```
gcc ctg gac ctg gat gct ggc ctg gag ccc agc cca ggc cta gag gac      1248
Ala Leu Asp Leu Asp Ala Gly Leu Glu Pro Ser Pro Gly Leu Glu Asp
                405                 410                 415 cca ctc ttg gat gca ggg acc aca gtc ctg tcc tgt ggc tgt gtc tca      1296
Pro Leu Leu Asp Ala Gly Thr Thr Val Leu Ser Cys Gly Cys Val Ser
            420                 425                 430 gct ggc agc cct ggg cta gga ggg ccc ctg gga agc ctc ctg gac aga      1344
Ala Gly Ser Pro Gly Leu Gly Gly Pro Leu Gly Ser Leu Leu Asp Arg
        435                 440                 445 cta aag cca ccc ctt gca gat ggg gag gac tgg gct ggg gga ctg ccc      1392
Leu Lys Pro Pro Leu Ala Asp Gly Glu Asp Trp Ala Gly Gly Leu Pro
    450                 455                 460 tgg ggt ggc cgg tca cct gga ggg gtc tca gag agt gag gcg ggc tca      1440
Trp Gly Gly Arg Ser Pro Gly Gly Val Ser Glu Ser Glu Ala Gly Ser
465                 470                 475                 480 ccc ctg gcc ggc ctg gat atg gac acg ttt gac agt ggc ttt gtg ggc      1488
Pro Leu Ala Gly Leu Asp Met Asp Thr Phe Asp Ser Gly Phe Val Gly
                485                 490                 495 tct gac tgc agc agc cct gtg gag tgt gac ttc acc agc ccc ggg gac      1536
Ser Asp Cys Ser Ser Pro Val Glu Cys Asp Phe Thr Ser Pro Gly Asp
            500                 505                 510 gaa gga ccc ccc cgg agc tac ctc cgc cag tgg gtg gtc att cct ccg      1584
Glu Gly Pro Pro Arg Ser Tyr Leu Arg Gln Trp Val Val Ile Pro Pro
        515                 520                 525 cca ctt tcg agc cct gga ccc cag gcc agc                              1614
Pro Leu Ser Ser Pro Gly Pro Gln Ala Ser
    530                 535

<210> SEQ ID NO 6
<211> LENGTH: 538
<212> TYPE: PRT
<213> ORGANISM: Homo sapiens

<400> SEQUENCE: 6

Met Pro Arg Gly Trp Ala Ala Pro Leu Leu Leu Leu Leu Gln Gly
 1               5                  10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
         35                 40                  45

Leu Thr Trp Gln Asp Gln Tyr Glu Glu Leu Lys Asp Glu Ala Thr Ser
     50                 55                  60

Cys Ser Leu His Arg Ser Ala His Asn Ala Thr His Ala Thr Tyr Thr
 65                 70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Lys Leu Ile
                165                 170                 175

Ser Val Asp Ser Arg Ser Val Ser Leu Leu Pro Leu Glu Phe Arg Lys
            180                 185                 190
```

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
            245                 250                 255

Thr His Pro Leu Trp Arg Leu Trp Lys Lys Ile Trp Ala Val Pro Ser
                260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
        290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535

<210> SEQ ID NO 7
<211> LENGTH: 153
<212> TYPE: PRT
<213> ORGANISM: Homo sapiens

<400> SEQUENCE: 7

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Asp Leu Gln Met Ile Leu Asn Gly Ile
    35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 8
<211> LENGTH: 153
<212> TYPE: PRT
<213> ORGANISM: Homo sapiens

<400> SEQUENCE: 8

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 9
<211> LENGTH: 162
<212> TYPE: PRT
<213> ORGANISM: Homo sapiens

<400> SEQUENCE: 9

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile

```
                        50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 10
<211> LENGTH: 144
<212> TYPE: PRT
<213> ORGANISM: Homo sapiens

<400> SEQUENCE: 10

Met Trp Leu Gln Ser Leu Leu Leu Leu Gly Thr Val Ala Cys Ser Ile
  1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide primer ZC22281

<400> SEQUENCE: 11
tgtgaatgac ttggtccctg aa                                      22

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer ZC22279

<400> SEQUENCE: 12
aacaggaaaa agctgaccac tca                                     23
```

```
<210> SEQ ID NO 13
<211> LENGTH: 31
<212> TYPE: DNA
<213> ORGANISM: Artificial Sequence
<220> FEATURE:
<223> OTHER INFORMATION: zalpha11 Ligand TaqMan probe, ZG32

<400> SEQUENCE: 13
tctgccagct ccagaagatg tagagacaaa c                                    31

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer ZC22277

<400> SEQUENCE: 14
ccaggagtgt ggcagctttc                                                 20

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer ZC22276

<400> SEQUENCE: 15
gcttgccctt cagcatgtag a                                               21

<210> SEQ ID NO 16
<211> LENGTH: 23
<212> TYPE: DNA
<213> ORGANISM: Artificial Sequence
<220> FEATURE:
<223> OTHER INFORMATION: zalpha11 TaqMan(r) probe, designated ZG31

<400> SEQUENCE: 16
cggctccccc tttcaacgtg act                                             23

<210> SEQ ID NO 17
<211> LENGTH: 8
<212> TYPE: PRT
<213> ORGANISM: Artificial Sequence
<220> FEATURE:
<223> OTHER INFORMATION: OVA257-264 peptide

<400> SEQUENCE: 17

Ser Ile Ile Asn Phe Glu Lys Leu
 1               5
```

METHODS OF TREATING VIRAL INFECTIONS USING IL-21

REFERENCE TO RELATED APPLICATIONS

This patent application is a continuation of U.S. patent application Ser. No. 11/553,367, filed Oct. 26, 2006 now abandoned; which is a continuation of U.S. patent application Ser. No. 10/456,262, filed Jun. 6, 2003 now abandoned; which claims benefit of U.S. Provisional Application Ser. No. 60/387,127, filed on Jun. 7, 2002, and are incorporated by reference herein.

BACKGROUND OF THE INVENTION

Cytokines generally stimulate proliferation or differentiation of cells of the hematopoietic lineage or participate in the immune and inflammatory response mechanisms of the body. Examples of cytokines which affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer. Other cytokines are involved in inflammatory responses, viral immunity, intracellular parasite immunity, allograft rejection, humoral responses, helminth immunity and allergic responses. The cytokines that bind class II cytokine receptors include interferon-alfa (IFN-α) subtypes, interferon-beta (IFN-β), interferon-gamma (IFN-γ), IL-10, IL-19 (U.S. Pat. No. 5,985,614), MDA-7 (Jiang et al., Oncogene 11, 2477-2486, (1995)), IL-20 (Jiang et al., Oncogene 11, 2477-2486, (1995)), IL-22 (Xie et al., J. Biol. Chem. 275, 31335-31339, (2000)), and AK-155 (Knappe et al., J. Virol. 74, 3881-3887, (2000)).

In particular, interleukins are a family of cytokines that mediate immunological responses. Central to an immune response is the T cell, which produce many cytokines and effect adaptive immunity to antigens. Mature T cells can be activated, i.e., by an antigen or other stimulus, to produce, for example, cytokines, biochemical signaling molecules, or receptors that further influence the fate of the T cell population.

B cells can be activated via receptors on their cell surface including the B cell antigen receptor and other accessory molecules to produce antibodies and perform accessory cell functions, such as the production of cytokines.

Natural killer (NK) cells have a common progenitor cell with T cells and B cells, and play a role in immune surveillance. NK cells, which comprise up to 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells without activation.

In particular, interleukins are a family of cytokines that mediate immunological responses. Central to an immune response is the T cell, which produce many cytokines and effect adaptive immunity to antigens. Mature T cells can be activated, i.e., by an antigen or other stimulus, to produce, for example, cytokines, biochemical signaling molecules, or receptors that further influence the fate of the T cell population.

Viral infections can be classified in various ways. For example, viruses may be classified phylogenetically, according to the infected target cell or organ, or by the disease state they induce. However, not all viruses and viral diseases are treated identically because additional factors, such as whether an infection is acute or chronic and the patient's underlying health, influence the type of treatment that is recommended. Generally, treatment of acute infections in immunocompetent patients should reduce the disease's severity, complications, and decrease the rate of transmission, making safety, cost, and convenience essential considerations in recommending an antiviral agent. Treatments for chronic infections should prevent viral damage to organs such as liver, lungs, heart, central nervous system, and gastrointestinal system, making efficacy the primary consideration.

There are few effective treatments for hepatitis. For the treatment of hepatitis B virus (HBV) and hepatitis C virus (HCV), the FDA has approved administration of recombinant interferon alpha (IFN-α). However, IFN-α is associated with a number of dose-dependent adverse effects, including thrombocytopenia, leukopenia, bacterial infections, and influenza-like symptoms. Other agents used to treat chronic HBV or HCV include the nucleoside analog RIBAVIRIN™ and ursodeoxycholic acid; however, neither has been shown to be very effective. RIBAVIRIN™+IFN combination therapy results in 47% rate of sustained viral clearance (Lanford, R. E. and Bigger, C. Virology 293: 1-9 (2002). (See, Medicine, (D. C. Dale and D. D. Federman, eds.) (Scientific American, Inc., New York), 4:VIII:1-8 (1995)).

Progressive chronic liver disease as a result of chronic infections, such as HCV and HBV, and tumorigenesis associated with HIV are three examples of diseases that can be treated with intervention therapy and/or preventative therapy using the methods of the present invention. The present invention provides methods for treating infections, particularly viral infections, by administering IL-21 to the subject. In certain embodiments, the IL-21 can be administered in conjunction with other antiviral compounds.

The present invention is also based on the discovery that IL-21 has antimicrobial and antiviral activity against specific acute infections such as influenza and specific chronic infections such as hepatitis. These antiviral effects may be mediated through immune system cells, such as cytotoxic T cells and NK cells. In the description and examples which follow, animals models and in vitro assay demonstrate the antiviral activities of Il-21. These and other uses should be apparent to those skilled in the art from the teachings herein.

SUMMARY OF THE INVENTION

In another aspect, the methods of the present invention provide a method of treating an infection comprising administering a therapeutically effective amount of a polypeptide having a functional activity of IL-21, wherein the infection is selected from the group of hepatitis B virus, hepatitis C virus, human immunodeficiency virus, sudden acute respiratory syndrome caused by a coronavirus, Herpes Simplex viruses, Epstein-Barr virus, Cytomegalovirus; Pox viruses; Papilloma virus; Adenovirus, Poliovirus; Orthomyxoviruses, Paramyxoviruses, Influenza viruses; caliciviruses; rabies viruses, and rinderpest viruses.

In another aspect, the present invention provides a method of treating a viral infection in a mammal comprising administering a therapeutically effective amount of a polypeptide having a functional activity of IL-21, wherein the viral infection results in a disease selected from the group consisting of Acquired immunodeficiency; Hepatitis; Gastroenteritis;

Hemorrhagic diseases; Enteritis; Carditis; Encephalitis; Paralysis; Bronchiolitis; Upper or lower respiratory disease; Respiratory Papillomatosis; Arthritis; Disseminated disease, Meningitis, and Mononucleosis.

In one aspect, the present invention provides a method of treating an infection comprising administering a therapeutically effective amount of a fusion protein comprising a first polypeptide having a functional activity of IL-21 and a second polypeptide, wherein the infection is selected from the group of hepatitis B virus, hepatitis C virus, human immunodeficiency virus, sudden acute respiratory syndrome caused by a coronovirus, Herpes Simplex viruses, Epstein-Barr virus, Cytomegalovirus; Pox viruses; Papilloma virus; Adenovirus, Poliovirus; Orthomyxoviruses, Paramyxoviruses, Influenza viruses; caliciviruses; rabies viruses, and rinderpest viruses.

In certain embodiments, the methods of treating viral infections using polypeptides and fusion proteins having a functional activity of IL-21, the level of viral infection is reduced. In other embodiments, the reduction in the level of viral infection is measured as reduction in viral load, increased viral-specific antibodies, reduction in alanine aminotransferase level (ALT), or histologic improvement in a target tissue as measured by immunohistochemistry.

The present invention also provides a method of treating a bacterial infection in a mammal comprising administering a therapeutically effective amount of a polypeptide having a functional activity of IL-21, wherein the bacterial infection is an infection by a bacteria selected from the group consisting of chlamydiae, listeriae, *helicobacter pylori, mycobacterium, mycoplasma, salmonella*, and *shigella*.

In other aspects, the present invention provides a method of treating a bacterial infection in a mammal comprising administering a therapeutically effective of a fusion protein comprising a first polypeptide that has the functional activity of IL-21 and a second polypeptide, wherein the bacterial infection is an infection by a bacteria selected from the group consisting of chlamydiae, listeriae, *helicobacter pylori, mycobacterium, mycoplasma, salmonella*, and *shigella*.

For all aspects and embodiments of the present invention, the polypeptide or first polypeptide in a fusion protein can comprise a polypeptide has at least 80%, 90%, 95% or complete identity to an IL-21 polypeptide comprising residues 41 (Gln) to 148 (Ile) of SEQ ID NO:2 or residues 32 (Gln) to 162 (Ser) of SEQ ID NO:2.

DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, an increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery that administration of IL-21 results in antiviral activity, thereby limiting the pathological effects caused by exposure to or infection by certain viral agents. In the examples which follow, animal models and in vitro assays demonstrate the activity of IL-21 on virally infected biological samples and T-cell immunity, in particular cytotoxic T-lymphocytes.

A. Description of IL-21 and its Receptor.

Human IL-21 (SEQ ID NO:1 and SEQ ID NO:2) was designated IL-21, and is described in commonly-owned U.S. Pat. No. 6,307,024, which is incorporated herein by reference. The IL-21 receptor, (previously designated zalpha11) now designated IL-21R (SEQ ID NO:5 and SEQ ID NO:6), and heterodimeric receptor IL-21R/IL-2Rγ are described in commonly-owned WIPO Publication Nos. WO 0/17235 and WO 01/77171, which are incorporated herein by reference. As described in these publications, IL-21 was isolated from a cDNA library generated from activated human peripheral blood cells (hPBCs), which were selected for CD3. CD3 is a cell surface marker unique to cells of lymphoid origin, particularly T cells.

The amino acid sequence for the IL-21R indicated that the encoded receptor belonged to the Class I cytokine receptor subfamily that includes, but is not limited to, the receptors for IL-2, IL-4, IL-7, IL-15, EPO, TPO, GM-CSF and G-CSF (for a review see, Cosman, "The Hematopoietin Receptor Superfamily" in *Cytokine* 5(2): 95-106, 1993). The tissue distribution of the receptor suggests that a target for IL-21 is hematopoietic lineage cells, in particular lymphoid progenitor cells and lymphoid cells. Other known four-helical-bundle cytokines that act on lymphoid cells include IL-2, IL-4, IL-7, and IL-15. For a review of four-helical-bundle cytokines, see, Nicola et al., *Advances in Protein Chemistry* 52:1-65, 1999 and Kelso, A., *Immunol. Cell Biol.* 76:300-317, 1998.

For IL-21, the secretory signal sequence is comprised of amino acid residues 1 (Met) to 31 (Gly), and the mature polypeptide is comprised of amino acid residues 32 (Gln) to 162 (Ser) (as shown in SEQ ID NO: 2). In general, cytokines are predicted to have a four-alpha helix structure, with helices A, C and D being most important in ligand-receptor interactions, and are more highly conserved among members of the family. Referring to the human IL-21 amino acid sequence shown in SEQ ID NO:2, an alignment of human IL-21, human IL-15, human IL-4, and human GM-CSF amino acid sequences predicted that IL-21 helix A is defined by amino acid residues 41-56; helix B by amino acid residues 69-84; helix C by amino acid residues 92-105; and helix D by amino acid residues 135-148; as shown in SEQ ID NO: 2. Structural analysis suggests that the A/B loop is long, the B/C loop is short and the C/D loop is parallel long. This loop structure results in an up-up-down-down helical organization. The cysteine residues are absolutely conserved between IL-21 and IL-15. The cysteine residues that are conserved between IL-15 and IL-21 correspond to amino acid residues 71, 78, 122 and 125 of SEQ ID NO: 2. Conservation of some of the cysteine residues is also found in IL-2, IL-4, GM-CSF and IL-21 corresponding to amino acid residues 78 and 125 of SEQ ID NO: 2. Consistent cysteine placement is further confirmation of the four-helical-bundle structure. Also highly conserved in the family comprising IL-15, IL-2, IL-4, GM-CSF and IL-21 is the Glu-Phe-Leu sequence as shown in SEQ ID NO: 2 at residues 136-138. Further analysis of IL-21 based on multiple alignments predicts that amino acid residues 44, 47 and 135 (as shown in SEQ ID NO: 2) play an important role in IL-21 binding to its cognate receptor. Moreover, the predicted amino acid sequence of murine IL-21 (SEQ ID NO:4) shows 57% identity to the predicted human protein. Based on comparison between sequences of human and murine IL-21 well-conserved residues were found in the regions predicted to encode alpha helices A and D.

The corresponding polynucleotides encoding the IL-21 polypeptide regions, domains, motifs, residues and sequences described herein are as shown in SEQ ID NO:1. The amino acid residues comprising helices A, B, C, and D, and loops A/B, B/C and C/D for IL-21, IL-2, IL-4, IL-15 and GM-CSF are shown in Table 1.

TABLE 1

| | Helix A | A/B Loop | Helix B | B/C Loop | Helix C | C/D Loop | Helix D | |
|---|---|---|---|---|---|---|---|---|
| IL-21 residues | 41-56 | 57-68 | 69-84 | 85-91 | 92-105 | 106-134 | 135-148 | SEQ ID NO: 2 |
| IL-2 residues | 36-46 | 47-52 | 53-75 | 76-86 | 87-99 | 100-102 | 103-121 | SEQ ID NO: 5 |
| IL-4 residues | 29-43 | 44-64 | 65-83 | 84-94 | 95-118 | 119-133 | 134-151 | SEQ ID NO: 6 |
| IL-15 residues | 45-68 | 69-83 | 84-101 | 102-106 | 107-119 | 120-133 | 134-160 | SEQ ID NO: 7 |
| GM-CSF residues | 30-44 | 45-71 | 72-81 | 82-90 | 91-102 | 103-119 | 120-131 | SEQ ID N0: 8 |

Those skilled in the art will recognize that the sequence disclosed in SEQ ID NO:1 represents a single allele of human IL-21 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the IL-21 polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated IL-21 polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95%, or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues 1 to 162 or 33 to 162 of SEQ ID NO:2. The present invention further includes nucleic acid molecules that encode such polypeptides. Methods for determining percent identity are described below.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 2 (amino acids are indicated by the standard one-letter codes).

$$\frac{\text{Total number of identical matches}}{\begin{bmatrix}\text{length of the longer sequence plus the number}\\ \text{of gaps introduced into the longer}\\ \text{sequence in order to align the two sequences}\end{bmatrix}} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant IL-21. The FASTA algorithm is described by Pearson and Lipman, *Proc. Nat'l Acad. Sci. USA* 85:2444 (1988), and by Pearson, *Meth. Enzymol.* 183:63 (1990).

Variant IL-21 polypeptides or polypeptides with substantially similar sequence identity are characterized as having one or more amino acid substitutions, deletions or additions. These changes are preferably of a minor nature, that is conservative amino acid substitutions (see Table 3) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 108 to 216 amino acid residues that comprise a sequence that is at least 80%, preferably at least 90%, and more preferably 95%, 96%, 97%, 98%, 99% or more identical to the corresponding region of SEQ ID NO:2. Polypeptides comprising affinity tags can further comprise a proteolytic cleavage site between the IL-21 polypeptide and the affinity tag. Preferred such sites include thrombin cleavage sites and factor Xa cleavage sites.

TABLE 3

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in IL-21 polypeptides so as to minimize disruption of higher order structure essential to biological activity. For example, where the IL-21 polypeptide comprises one or more helices, changes in amino acid residues will be made so as not to disrupt the helix geometry and other components of the molecule where changes in conformation abate some critical function, for example, binding of the molecule to its binding partners, e.g., A and D helices, residues 44, 47 and 135 of SEQ ID NO: 2.

The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichroism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the IL-21 protein sequence as shown in SEQ ID NO:2 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in IL-21, hydrophilic regions include amino acid residues 114-119 of SEQ ID NO: 2, amino acid residues 101-105 of SEQ ID NO: 2, amino acid residues 126-131 of SEQ ID NO: 2, amino acid residues 113-118 of SEQ ID NO: 2, and amino acid residues 158-162 of SEQ ID NO: 2.

Those skilled in the art will recognize that hydrophilicity or hydrophobicity will be taken into account when designing modifications in the amino acid sequence of a IL-21 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include residues 100 and 103 as shown in SEQ ID NO: 2. Cysteine residues at positions 71, 78, 122 and 125 of SEQ ID NO: 2, will be relatively intolerant of substitution.

The identities of essential amino acids can also be inferred from analysis of sequence similarity between IL-15, IL-2, IL-4 and GM-CSF with IL-21. Using methods such as "FASTA" analysis described previously, regions of high similarity are identified within a family of proteins and used to analyze amino acid sequence for conserved regions. An alternative approach to identifying a variant IL-21 polynucleotide on the basis of structure is to determine whether a nucleic acid molecule encoding a potential variant IL-21 gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also includes administration of molecules having the functional activity of IL-21. Thus, administration of functional fragments and functional modified polypeptides of IL-21 polypeptides and nucleic acid molecules encoding such functional fragments and modified polypeptides. A "functional" IL-21 or fragment thereof as defined herein is characterized by its proliferative or differentiating activity, by its ability to induce or inhibit specialized cell functions, in particular for immune effector cells, such as NK cells, T cells, B cells and dendritic cells. Functional IL-21 also includes the ability to exhibit anti-cancer and anti-viral effects in vitro or in vivo, or by its ability to bind specifically to an anti-IL-21 antibody or IL-21 receptor (either soluble or immobilized). As previously described herein, IL-21 is characterized by a four-helical-bundle structure comprising helix A (amino acid residues 41-56), helix B (amino acid residues 69-84), helix C (amino acid residues 92-105) and helix D (amino acid residues 135-148), as shown in SEQ ID NO: 2. Thus, the present invention further provides fusion proteins encompassing: (a) polypeptide molecules comprising one or more of the helices described above; and (b) functional fragments comprising one or more of these helices. The other polypeptide portion of the fusion protein can contributed by another four-helical-bundle cytokine, such as IL-15, IL-2, IL-4 and GM-CSF, or by a non-native and/or an unrelated secretory signal peptide that facilitates secretion of the fusion protein.

Routine deletion analyses of nucleic acid molecules can be performed to obtain functional fragments of a nucleic acid molecule that encodes a IL-21 polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for IL-21 activity, or for the ability to bind anti-IL-21 antibodies or zalpha11 receptor. One alternative to exonuclease digestion is to use oligonucleotide-directed mutagenesis to introduce deletions or stop codons to specify production of a desired IL-21 fragment. Alternatively, particular fragments of a IL-21 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204), and region-directed mutagenesis (Derbyshire et al., *Gene* 46:145 (1986), and Ner et al., *DNA* 7:127, (1988)).

Variants of the disclosed IL-21 nucleotide and polypeptide sequences can also be generated through DNA shuffling as disclosed by Stemmer, *Nature* 370:389 (1994), Stemmer, *Proc. Natl Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-21 antibodies or soluble zalpha11 receptor, can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multifunctional molecules. For example, one or more helices from IL-21 can be joined to other cytokines to enhance their biological properties or efficiency of production.

The present invention thus provides a series of novel, hybrid molecules in which a segment comprising one or more of the helices of IL-21 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202: 301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993). It can advantageous to stabilize IL-21 to extend the half-life of the molecule, particularly for extending metabolic persistence in an active state. To achieve extended half-life, IL-21 molecules can be chemically modified using methods described herein. PEGylation is one method commonly used that has been demonstrated to increase plasma half-life, increased solubility, and decreased antigenicity and immunogenicity (Nucci et al., *Advanced Drug Delivery Reviews* 6:133-155, 1991 and Lu et al., *Int. J. Peptide Protein Res.* 43:127-138, 1994).

A limited number of non-conservative amino acids, amino acids that are not encoded by the genetic code, non-naturally occurring amino acids, and unnatural amino acids can be substituted for IL-21 amino acid residues.

The present invention also provides polypeptide fragments or peptides comprising an epitope-bearing portion of a IL-21 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential (Hopp et al., 1981, ibid. and Hopp, 1986, ibid.). In IL-21 these regions include: amino acid residues 114-119, 101-105, 126-131, 113-118, and 158-162 of SEQ ID NO: 2.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:4. Such epitope-bearing peptides and polypeptides can be produced by fragmenting a IL-21 polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

Regardless of the particular nucleotide sequence of a variant IL-21 polynucleotide, the polynucleotide encodes a polypeptide that is characterized by its proliferative or differentiating activity, its ability to induce or inhibit specialized cell functions, or by the ability to bind specifically to an anti-IL-21 antibody or zalpha11 receptor. More specifically, variant IL-21 polynucleotides will encode polypeptides which exhibit at least 50% and preferably, greater than 70%, 80% or 90%, of the activity of the polypeptide as shown in SEQ ID NO: 2.

For any IL-21 polypeptide, including variants and fusion proteins, one of ordinary skill in the art can readily generate a fully degenerate polynucleotide sequence encoding that variant using the genetic code and methods known in the art.

The present invention further provides a variety of other polypeptide fusions (and related multimeric proteins comprising one or more polypeptide fusions). For example, a IL-21 polypeptide can be prepared as a fusion to a dimerizing protein as disclosed in U.S. Pat. Nos. 5,155,027 and 5,567, 584. Preferred dimerizing proteins in this regard include immunoglobulin constant region domains. Immunoglobulin-IL-21 polypeptide fusions can be expressed in genetically engineered cells (to produce a variety of multimeric IL-21 analogs). Auxiliary domains can be fused to IL-21 polypeptides to target them to specific cells, tissues, or macromolecules. For example, a IL-21 polypeptide or protein could be targeted to a predetermined cell type by fusing a IL-21 polypeptide to a ligand that specifically binds to a receptor on the surface of that target cell. In this way, polypeptides and proteins can be targeted for therapeutic or diagnostic purposes. A IL-21 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Using the methods discussed herein, one of ordinary skill in the art can identify and/or prepare a variety of polypeptides that have substantially similar sequence identity to residues 1-162 or 33-162 of SEQ ID NO: 2, or functional fragments and fusions thereof, wherein such polypeptides or fragments or fusions retain the properties of the wild-type protein such as the ability to stimulate proliferation, differentiation, induce specialized cell function or bind the IL-21 receptor or IL-21 antibodies.

The IL-21 polypeptides used in the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a IL-21 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a IL-21 polypeptide into the secretory pathway of a host cell, a secretory signal sequence (also known as a leader sequence, prepro sequence or pre sequence) is provided in the expression vector. The secretory signal sequence may be that of IL-21, or may be derived from another secreted protein (e.g., t-PA) or synthesized de novo. The secretory signal sequence is operably linked to the IL-21 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996).

A wide variety of suitable recombinant host cells includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308,

*E. coli* K12 C600, *E. coli* HB101, *E. coli* K12 C600 R.sub.k-M.sub.k-, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*. Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, 3$^{rd}$ Edition (John Wiley & Sons 1995); Wu et al., *Methods in Gene Biotechnology* (CRC Press, Inc. 1997)). In one embodiment, the methods of the present invention use IL-21 expressed in the W3110 strain, which has been deposited at the American Type Culture Collection (ATCC) as ATCC #27325.

When large scale production of IL-21 using the expression system of the present invention is required, batch fermentation can be used. Generally, batch fermentation comprises that a first stage seed flask is prepared by growing *E. coli* strains expressing IL-21 in a suitable medium in shake flask culture to allow for growth to an optical density (OD) of between 5 and 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferrous sulfate or ferrous chloride, and other trace elements. Growth medium can be supplemented with carbohydrates, such as fructose, glucose, galactose, lactose, and glycerol, to improve growth. Alternatively, a fed batch culture is used to generate a high yield of IL-21 protein. The IL-21 producing *E. coli* strains are grown under conditions similar to those described for the first stage vessel used to inoculate a batch fermentation.

Following fermentation the cells are harvested by centrifugation, re-suspended in homogenization buffer and homogenized, for example, in an APV-Gaulin homogenizer (Invensys APV, Tonawanda, N.Y.) or other type of cell disruption equipment, such as bead mills or sonicators. Alternatively, the cells are taken directly from the fermentor and homogenized in an APV-Gaulin homogenizer. The washed inclusion body prep can be solubilized using guanidine hydrochloride (5-8 M) or urea (7-8 M) containing a reducing agent such as beta mercaptoethanol (10-100 mM) or dithiothreitol (5-50 mM). The solutions can be prepared in Tris, phosphate, HEPES or other appropriate buffers. Inclusion bodies can also be solubilized with urea (2-4 M) containing sodium lauryl sulfate (0.1-2%). In the process for recovering purified IL-21 from transformed *E. coli* host strains in which the IL-21 is accumulates as refractile inclusion bodies, the cells are disrupted and the inclusion bodies are recovered by centrifugation. The inclusion bodies are then solubilized and denatured in 6 M guanidine hydrochloride containing a reducing agent. The reduced IL-21 is then oxidized in a controlled renaturation step. Refolded IL-21 can be passed through a filter for clarification and removal of insoluble protein. The solution is then passed through a filter for clarification and removal of insoluble protein. After the IL-21 protein is refolded and concentrated, the refolded IL-21 protein is captured in dilute buffer on a cation exchange column and purified using hydrophobic interaction chromatography.

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

A variety of assays known to those skilled in the art can be utilized to detect antibodies which bind to IL-21 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant IL-21 protein or polypeptide.

The methods of the present invention also contemplate using chemically modified IL-21 compositions, in which a IL-21 polypeptide is linked with a polymer. Illustrative IL-21 polypeptides are soluble polypeptides that lack a functional transmembrane domain, such as a mature IL-21 polypeptide. Typically, the polymer is water soluble so that the IL-21 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce IL-21 conjugates.

IL-21 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-21 conjugate can also comprise a mixture of such water-soluble polymers.

B. The Use of IL-21 for Infections

One requirement for achieving sustained immunity and durable clinical responses is the amplification in the numbers and activity of the cells that suppress viral replication, prevent reinfection and kill infected cells. Thus, new factors that mediate effects on lymphocytes including cytotoxic T-cells (CTLs), NK cells, and B-cells, as well myeloid cells such as neutrophils and monocytic cells will improve antiviral activity by the immune system. IL-21 is a product of activated CD4$^+$ "helper" T-cells which are required for both humoral and cell-mediated immunity and for sustaining long-term memory to antigenic re-challenge (U.S. Pat. No. 6,307,024; Parrish-Novak J et al., *Nature* 408:57-63, 2000). The receptor for IL-21 is expressed on cells that mediate antiviral responses and previous experiments have shown that IL-21 can stimulate the proliferation of these cell types in vitro (WIPO Publication Nos. WO 0/17235 and WO 01/77171). Additional experiments affirm these IL-21 activities in vivo.

A central role of the immune system is to protect against microbial infection (reviewed by Paul, W E (Ed), *Fundamental Immunology*. Lippincott-Raven, New York, N.Y., 1999). The immune system makes a rapid and highly specific response to a broad spectrum of bacteria, parasites and viruses through an orchestration of cellular interactions and synthesis of soluble factors including cytokines. Two categories of activity describe this protective response: Innate and adaptive immunity. The innate immune response is an acute response and functions to limit pathogen replication. Macrophages, dendritic cells, NK cells and neutrophilic granulocytes constitute some of the cell type responsible for this activity. Innate immunity is accompanied by a more protracted response, the adaptive immune response, whereby an antigen-specific effector system regulated by dendritic cells, T-cells and B-cells mediates resolution of infection and long term memory.

Cytokines play a major role in regulating immune responses to infection. For instance, IFN-($\alpha$ and -$\gamma$ are critical for inhibiting virus replication and preventing the replication of cells that harbor virus (reviewed by Vilcek J. and Sen G C, B N, Knipe D M, Howley P M. (Eds.), *Interferons and other cytokines. Fields Fundamental Virology.*, $3^{rd}$ ed., Lippincott-Raven Publishers Philadelphia, Pa., 1996, pages 341-365). IFN's also stimulate cells regulating innate immunity and are required for the initiation of the acquired immune response. Additional cytokines produced at early times during viral infection include NK cell-produced IFN-$\gamma$, tumor necrosis factor-$\alpha$, and IL-15. These molecules help shape inflammatory responses to infection as well as stimulate the proliferation and differentiation of lymphocytes critical for adaptive immunity. With respect to viral infection, the CD4+ T-cells that become activated in response to viral antigens initiate a T-helper type 1 (TH1) response and the subsequent cascade required for cell-mediated immunity. That is, following their expansion by specific growth factors like the cytokine IL-2, these T-cells stimulate antigen-specific CD8+ T-cells, macrophages, and NK cells to kill virally infected host cells. Again, cytokines play an important role in mediating these types of responses. IFN-$\gamma$, for example, is critical for regulating the differentiation of a Th1 T-cells and for stimulating cell-mediated immunity (reviewed by Paul, W E supra.).

Strategies for treating infectious disease often focus on ways to enhance immunity. For instance, the most common method for treating viral infection involves prophylactic vaccines that induce immune-based memory responses. Many endemic childhood diseases such as measles, chicken pox, and mumps are now quite rare in the U.S. thanks to aggressive vaccination programs (Dowdle W R, and Orenstein W A, *Proc Nat. Acad. Sci. USA.* 91:2464-8, 1994). Another method for treating viral infection includes passive immunization via immunoglobulin therapy such as infusing antibodies to respiratory syncytial virus (RSV), into high risk patients (Meissner H C, *J. Pediatr.* 124:S17-21, 1994). IFN-$\alpha$ is another method for treating viral infections such as genital warts (Reichman R C et al., *Ann. Intern. Med.* 108:675-9, 1988) and chronic diseases like HCV (Davis G L et al., *New Engl. J. Med.* 339:1493-9, 1998) and HBV. Although oftentimes efficacious, these methods have limitations in clinical use. For instance, many viral infections are not amenable to vaccine development, nor are they treatable with antibodies alone. In addition, IFN's are not extremely effective and they can cause significant toxicities; thus, there is a need for improved therapies.

Improved methods for treating diseases such as viral infections are dependent on the isolation of reagents that specifically enhance innate and acquired immunity; compounds that stimulate the effector cells of an antiviral response. We have previously reported the discovery of IL-21 (Parrish-Novak J et al., supra; U.S. Pat. No. 6,307,024). This cytokine is produced by activated CD4+ T-cells. The IL-21 receptor is expressed by a variety of cells within the immune system such as CD4+ and CD8+ T-cells, B-cells, NK cells, and dendritic cells. Like IL-2, IL-21 acts as an autocrine factor that drives T-cell proliferation, a critical requirement for amplifying an antiviral response. In addition, IL-21 enhances the proliferation and killing activities of both CD8 T-cells and NK cells, thus demonstrating an important role in cell-mediated immunity (Parrish-Novak, J. et al., supra.; U.S. Pat. No. 6,307,024; and Kasaian M T et al., *Immunity* 16:559-69, 2002). Finally, IL-21 enhances the proliferation of B-cells in the presence of T-cell help, thereby suggesting an important role in stimulating antibody-mediated processes (Parrish-Novak, J. et al., supra.; U.S. Pat. No. 6,307,024). In addition, data described herein have shown not only the immunostimulatory effects of IL-21 on the immune system in regard to CTLs, but also IL-21 is immunostimulatory and represents a novel treatment for viral disease.

The IL-21 polypeptides of the present invention are shown to stimulate CTL and NK cells. IL-21 can hence be used in therapeutic antiviral applications in humans. As such, IL-21 antiviral activity is useful in the treatment and prevention of human viral infections. Examples of the types of viral infections for IL-21 use include, but are not limited to: infections caused by DNA Viruses (e.g., Herpes Viruses such as Herpes Simplex viruses, Epstein-Barr virus, Cytomegalovirus; Pox viruses such as Variola (small pox) virus; Hepadnaviruses (e.g, Hepatitis B virus); Papilloma viruses; Adenovinises); RNA Viruses (e.g., HIV I, II; HTLV I, II; Poliovirus; Hepatitis A; coronoviruses, such as sudden acute respiratory syndrome (SARS); Orthomyxoviruses (e.g., Influenza viruses); Paramyxoviruses (e.g., Measles virus); Rabies virus; Hepatitis C virus), Flaviviruses, Influenza viruses; caliciviruses; rabies viruses, rinderpest viruses, Arena virus, and the like. Moreover, examples of the types of virus-related diseases for which IL-21 could be used include, but are not limited to: Acquired immunodeficiency; Hepatitis; Gastroenteritis; Hemorrhagic diseases; Enteritis; Carditis; Encephalitis; Paralysis; Bronchiolitis; Upper and lower respiratory disease; Respiratory Papillomatosis; Arthritis; Disseminated disease, Meningitis, Mononucleosis. In addition, IL-21 can be used in various applications for antiviral immunotherapy, and in conjunction with other cytokines, other protein or small molecule antivirals, and the like.

Moreover, IL-21 will be useful treatment of other microbial infections. These types of microbes include bacteria and fungus. Specific bacterial infections that can be treated with IL-21, include but are not limited to, chlamydiae, listeriae, *helicobacter pylori, mycobacterium, mycoplasma, bacillus anthracis, salmonella*, and *shigella*. An example of a fungal infection include, but are not limited to, candidiasis.

For example:

(1) IL-21 can be used as a monotherapy for acute and chronic viral infections and for immunocompromised patients. Methods that enhance immunity can accelerate the recovery time in patients with unresolved infections. A partial list of the types of infections is provided (see above). Immunotherapies can have an even greater impact on subsets of immunocompromised patients such as the very young or elderly as well as patients that suffer immunodeficiencies acquired through infection, or induced following medical interventions such as chemotherapy or bone marrow ablation. Examples of the types of indications being treated via immune-modulation include; the use of IFN-α for chronic hepatitis (Perry C M, and Jarvis B. *Drugs* 61:2263-88, 2001), the use of IL-2 following HIV infection (Mitsuyasu R., *J Infect Dis.* 185 Suppl 2:S115-22, 2002; and Ross R W et al., *Expert Opin Biol Ther.* 1:413-24, 2001), and the use of either interferon (Faro A, *Springer Semin Immunopathol.* 20:425-36, 1998) for treating Epstein Barr Virus infections following transplantation. Experiments performed in animal models indicate that IL-2 and GM-CSF may also be efficacious for treating EBV related diseases (Baiocchi R A et al. *J Clin. Invest.* 108:887-94, 2001).

(2) IL-21 can be used in combination with antiviral agents. Some of the more common treatments for viral infection include drugs that inhibit viral replication such as ACYCLOVIR™. In addition, the combined use of some of these agents form the basis for highly active antiretroviral therapy (HAART) used for the treatment of HIV. Examples in which the combination of immunotherapy (ie cytokines) and antiviral drugs shows improved efficacy include the use of interferon plus RIBAVIRIN™ for the treatment of chronic HCV infection (Maddrey W C, *Semin. Liver. Dis.* 19 Suppl 1:67-75, 1999) and the combined use of IL-2 and HAART (Ross, R W et al, ibid.) Thus, as IL-21 can stimulate the immune system against disease, it can similarly be used in combination with HAART and other antiviral drugs.

In particular, IL-21 may be useful in monotherapy or combination therapy with IFN-α (with or without RIBAVIRIN™) in patients who do not respond well to IFN therapy. These patients may not respond to IFN therapy due to having less type I interferon receptor on the surface of their cells (Yatsuhashi et al. *J Hepatol June* 30(6):995-1003, 1999; Mathai et al., *J. Interferon Cytokine Res Sep.* 19(9):1011-8, 1999; Fukuda et al. *J Med Virol March* 63(3):220-7, 2001). IL-21 may also be useful in monotherapy or combination therapy with IFN-α (with or without RIBAVIRIN™) in patients who have less type I interferon receptor on the surface of their cells due to down-regulation of the type I interferon receptor after type I interferon treatment (Dupont S A, et al. *J. Interferon Cytokine Res.* April; 22(4):491-501, 2002).

(3) IL-21 can be used in combination with other immunotherapies including cytokines, immunoglobulin transfer, and various co-stimulatory molecules. In addition to antiviral drugs, IL-21 could be used in combination with any other immunotherapy that is intended to stimulate the immune system. Thus, IL-21 could be used with other cytokines such as Interferon or IL-2. IL-21 could also be added to methods of passive immunization that involve immunoglobulin transfer, one example bring the use of antibodies to treat RSV infection in high risk patients (Meissner H C, ibid.). In addition, IL-21 could be used with additional co-stimulatory molecules such as 4-1BB ligand that recognize various cell surface molecules like CD137 (Tan, J T et al., *J Immunol.* 163:4859-68, 1999).

(4) IL-21 can be used as an adjuvant for antiviral vaccines. The use of prophylactic vaccines for the prevention of viral disease is well known. IL-21 could be used as an adjuvant with these vaccines for indications where the efficacy of the vaccine is reduced, one example being the hepatitis B vaccine (Hasan M S et al., *J Infect Dis.* 180:2023-6, 1999; and Evans T G et al., *Clin Nephrol.* 54:138-42, 2000). In addition to prophylactic vaccines, therapeutic vaccines are being developed that are intended to arrest an ongoing infection. The methodologies for these vaccines are quite varied and include, but are not limited to, viral antigens delivered via DNA, viral peptides, viral proteins, portions of viral particles, and viral antigens loaded into cell-based therapies such as dendritic cells. Similar to the combined treatment of a therapeutic cancer with a cytokine like IL-2 (Shimizu K et al., *Proc. Nat. Acad. Sci. U S A.* 96:2268-73, 1999), IL-21 could be used in combination with a therapeutic antiviral vaccine.

The tissue distribution of a receptor for a given cytokine offers a strong indication of the potential sites of action of that cytokine. Northern analysis of IL-21 receptor revealed transcripts in human spleen, thymus, lymph node, bone marrow, and peripheral blood leukocytes. Specific cell types were identified as expressing IL-21 receptors, and strong signals were seen in a mixed lymphocyte reaction (MLR) and in the Burkitt's lymphoma Raji. The two monocytic cell lines, THP-1 (Tsuchiya et al., *Int. J. Cancer* 26:171-176, 1980) and U937 (Sundstrom et al., *Int. J. Cancer* 17:565-577, 1976), were negative.

As discussed herein, IL-21 may activate the immune system which is important in boosting immunity to infectious diseases, treating immunocompromised patients, such as HIV+ patients, or in improving vaccines. In particular, IL-21 stimulation or expansion of NK cells, or their progenitors, would provide therapeutic value in treatment of viral infection, and as an anti-neoplastic (anticancer) factor. NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998). Similarly, IL-21 stimulation of the immune response against viral and non-viral pathogenic agents (including bacteria, protozoa, and fungi) would provide therapeutic value in treatment of such infections by inhibiting the growth of such infections agents. Determining directly or indirectly the levels of a pathogen or antigen, such as a tumor cell, present in the body can be achieved by a number of methods known in the art and described herein. In general, a therapeutically effective amount of IL-21 includes an amount sufficient to produce a clinically significant change in virally infected mammals; such changes can include, but are not limited to, an amount of IL-21 sufficient to produce a clinically significant change in the level of CTLs or NK cells; an amount of IL-21 sufficient to produce a clinically significant change in viral load, and in anti-viral antibody titer. Determination of such clinically significant differences or changes is well within the skill of one in the art. The measurement of antiviral CTLs, NK cells, viral load and antiviral antibody titers have been studied after cytokine administration to both acute and chronic models of lymphocytic choriomeningitis virus (LCMV) infection in the mouse. (Blattman et al. supra) CTL measurements including enumeration, cytolytic activity, cytokine production and proliferation have been measured along with viral load in chronically infected HCV patients (Wedermeyer et al. *J. Immunol.* 169:3447-3458, 2002).

Clinically, diagnostic tests for HCV include serologic assays for antibodies and molecular tests for viral particles. Enzyme immunoassays are available (Vrielink et al., *Transfusion* 37:845-849, 1997), but may require confirmation using additional tests such as an immunoblot assay (Pawlotsky et al., *Hepatology* 27:1700-1702, 1998). Qualitative and quantitative assays generally use polymerase chain reaction techniques, and are preferred for assessing viremia and treatment response (Poynard et al., *Lancet* 352:1426-1432, 1998; McHutchinson et al., *N. Engl. J. Med.* 339:1485-1492, 1998). Several commercial tests are available, such as, quantitative RT-PCR (Amplicor HCV Monitor™, Roche Molecular Systems, Branchburg, N.J.) and a branched DNA (deoxyribonucleic acid) signal amplification assay (Quantiplex™ HCV RNA Assay [bDNA], Chiron Corp., Emeryville, Calif.). A non-specific laboratory test for HCV infection measures alanine aminotransferase level (ALT) and is inexpensive and readily available (National Institutes of Health Consensus Development Conference Panel, *Hepatology* 26 (Suppl. 1):2S-10S, 1997). Histologic evaluation of liver biopsy is generally considered the most accurate means for determining HCV progression (Yano et al., *Hepatology* 23:1334-1340, 1996.) For a review of clinical tests for HCV, see, Lauer et al., *N. Engl. J. Med.* 345:41-52, 2001.

There are several in vivo models for testing HBV and HCV that are known to those skilled in art. For example, the effects of IL-21 on mammals infected with HBV can accessed using a woodchuck model. Briefly, woodchucks chronically infected with woodchuck hepatitis virus (WHV) develop hepatitis and hepatocellular carcinoma that is similar to disease in humans chronically infected with HBV. The model has been used for the preclinical assessment of antiviral activity. A chronically infected WHV strain has been established and neonates are inoculated with serum to provide animals for studying the effects of certain compounds using this model. (For a review, see, Tannant et al., *ILAR J.* 42 (2):89-102, 2001). Chimpanzees may also be used to evaluate the effect of IL-21 on HBV infected mammals. Using chimpanzees, characterization of HBV was made and these studies demonstrated that the chimpanzee disease was remarkably similar to the disease in humans (Barker et al., *J. Infect. Dis.* 132:451-458, 1975 and Tabor et al., *J. Infect. Dis.* 147:531-534, 1983.) The chimpanzee model has been used in evaluating vaccines (Prince et al., In: *Vaccines* 97, Cold Spring Harbor Laboratory Press, 1997.) Therapies for HIV are routinely tested using non-human primates infected with simian immunodeficiency viruses (for a review, see, Hirsch et al., *Adv. Pharmcol.* 49:437-477, 2000 and Nathanson et al., *AIDS* 13 (suppl. A):S113-S120, 1999.) For a review of use of non-human primates in HIV, hepatitis, malaria, respiratory syncytial virus, and other diseases, see, Sibal et al., *ILAR J.* 42 (2):74-84, 2001.

For pharmaceutical use, the proteins of the present invention are formulated for parenteral, particularly intravenous or subcutaneous, delivery according to conventional methods. The bioactive polypeptide or antibody conjugates described herein can be delivered intravenously, intraarterially or intraductally, or can be introduced locally at the intended site of action. Intravenous administration will be by bolus injection or infusion over a typical period of one to several hours. In general, pharmaceutical formulations will include a IL-21 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 µg/kg per day, with the exact dose determined by the clinician according to accepted standards, taking into account the nature and severity of the condition to be treated, patient traits, etc. Determination of dose is within the level of ordinary skill in the art. The proteins can be administered for acute treatment, over one week or less, often over a period of one to three days or can be used in chronic treatment, over several months or years.

The present invention also contemplates chemically modified IL-21 compositions, in which a IL-21 polypeptide is linked with a polymer. Illustrative IL-21 polypeptides are soluble polypeptides that lack a functional transmembrane domain, such as a mature IL-21 polypeptide. Typically, the polymer is water soluble so that the IL-21 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce IL-21 conjugates.

IL-21 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-21 conjugate can also comprise a mixture of such water-soluble polymers.

PEGylation of IL-21 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)).

The present invention contemplates methods for treating cancer using compositions comprising an IL-21 polypeptide or polypeptide as described herein. Such compositions can further comprise a carrier. The carrier can be a conventional organic or inorganic carrier. Examples of carriers include water, buffer solution, alcohol, propylene glycol, macrogol, sesame oil, corn oil, and the like.

The invention is further illustrated by the following non-limiting examples.

EXAMPLES

Example 1

IL-21 Purified Recombinant Human Protein Dose-Response Study in Normal Mice

A. Summary

Normal six week old female C57Bl/6 (Harlan Sprague Dawley, Indianapolis, Ind.). mice were treated by intraperitoneal injection once daily for either four or eight days with one of four dose levels of purified recombinant human IL-21 (U.S. Pat. No. 6,307,024) at 0.1, 0.5, 5 or 50 µg/mouse/day or with vehicle as a control. Body weights and body temperatures were monitored daily. On either day four or day nine, four of the eight mice from each protein treatment group and five of the ten mice in the vehicle control group were sacrificed. Blood, bone marrow and tissues were harvested and analyzed. Potential perturbations in lymphoid tissues were examined, as well as general physiologic and toxicological parameters.

There was no evidence of toxicity of human IL-21 protein at any of the doses tested. Body weights and temperatures were unchanged. There were no apparent changes in clinical chemistry parameters. However, there were consistent findings relating to increased percentages of myeloid lineage cells in bone marrow, spleen and peripheral blood in mice treated with the highest dose of IL-21 compared to the vehicle control. There was a statistically significant increase in myeloid lineage sized cells identified by flow cytometric analysis of spleen homogenate in the high-dose group. The spleens of the two highest dose groups were statistically significantly larger than the other groups. On histopathologic examination, however, only a marginal increase in extramedullary hematopoiesis was seen in the highest dose group. There was a statistically significant increase in the myeloid to erythroid ratio of the bone marrow in the highest dose group compared to the other groups. Finally, there were increases seen in peripheral blood both in total white blood cell counts and in the percentage of monocytes in the same group.

B. Dosing Solution Preparation

Purified recombinant human IL-21 was diluted into sterile phosphate buffered saline (GibcoBRL, Grand Island, N.Y.) at concentrations to deliver 50, 5, 0.5 or 0.1 micrograms of protein in 0.1 ml of PBS vehicle. The doses for the first four days were made on day 0 and frozen in a frosty −20° C. freezer prior to use. The doses for days five through eight were made on day five and frozen as above. Aliquots of the same PBS were similarly frozen for the vehicle treated control group. On the day of administration the appropriate aliquots were thawed and 0.1 ml of solution was injected intraperitoneally into the mice each day for either four or eight days.

C. Study Design

The mice were six weeks old at the start of the study. Each treatment group consisted of eight mice, except for the vehicle control group that included ten mice. One half of the mice in each treatment group were sacrificed after four days of treatment and the other half after eight days.

Before treatment each day, each mouse was weighed and her body temperature recorded using the Portable Programmable Notebook System (BMDS, Inc, Maywood, N.J.), by scanning the mouse for identification number and body temperature from transponders implanted subcutaneously (IPTT-100, BMDS, Maywood, N.J.).

At sacrifice, tissues harvested to assess white blood cell populations by flow cytometric analysis included bone marrow, thymus and spleen. FACS analysis of the lymphoid organs and bone marrow was performed with the FACSCalibur, (Becton Dickinson, Mansfield, Mass.). The tissues harvested for histologic examination for signs of toxicity of the protein included: spleen, thymus, liver, kidney, adrenal gland, heart and lungs. All tissues fixed for histology were kept at 4° C. overnight in 10% Normal Buffered Saline (NBF) (Surgipath, Richmond, Ill.). The following day the NBF was replaced with 70% ethanol and the tissues returned to 4° C. until processing for histology.

The tissues were processed and stained for Hematoxylin and Eosin in house, then sent to a contract pathologist for histopathologic analysis. Blood was collected for complete blood cell counts (CBC) and serum chemistry profiles. The CBC's were analyzed in-house with the Cell Dyn 3500 Hematology Analyzer (Abbott Diagnostics Division, Abbott Park, Ill.) and manual differential white blood cell counts were analyzed at Phoenix Central Laboratory, (Everett, Wash.). The serum was kept frozen at −20° C. until submission to Phoenix Central Laboratory for complete serum chemistry panels. To assess myeloid:erythroid ratios, the bone marrow from one femur was applied to CytoSpin slides (CYTOSPIN 3 CYTOCENTRIFUGE and CYTO SLIDES, Shandon, Pittsburgh, Pa.) and sent to Phoenix Central Laboratories for analysis.

D. Study Results

There were no apparent clinical indications of physiologic effects or of toxicity of human IL-21 at doses of 50 µg/day or lower. Body weights and temperatures remained normal for the duration of the treatments. Serum chemistry parameters were in normal ranges. Red blood cell and platelet counts appeared normal. In the mice receiving 50 µg/day for 8 days, manual differential white blood cell counts showed that the percentage of monocytes was elevated in the peripheral blood, and an apparent increase in the total white blood cell counts. In bone marrow flushed from a femur, myeloid to erythroid ratios were increased in the 50 µg dose group, and to a lesser degree the 5 µg dose group from the 8-day dose set. In a non-parametric multiple column comparison using InStat (InStat MAC; GraphPad Software, Inc., San Diego, Calif.), this difference was statistically significant (p=0.0049). The difference between the highest dose group and vehicle was also significant, (p=0.0286). The increased white blood cells in peripheral blood and the significant increase in myeloid precursors in the marrow may thus be related.

Histologic evaluation of the following tissues showed no apparent evidence of cytologic or structural changes, mitotic events or necrosis: thymus, liver, kidney, adrenal gland, duodenum, pancreas, jejunum, caecum, colon, mesenteric lymph nodes, uterus, ovary, salivary gland, heart, trachea, lung, and brain. There were no apparent differences between the treatment groups in the weights of the thymus, kidney, liver or brain. Of all the tissues examined, only the spleen weights were significantly affected.

Each mouse spleen weight was normalized to her brain weight. In the 50 µg/day treatment group compared to the vehicle, 0.1 µg and 0.5 µg treatment groups, the average of the spleen weights was nearly 50% greater after four days of treatment and almost 100% greater after eight days than the average spleen weights of the other three groups. In the four-day set, the 5 µg/day group also tended to have larger spleens than the control and low dose groups. The difference in the spleen/brain weights with data from the four-day and the eight-day sets combined by treatment group was statistically significant (p=0.0072) by Kruskall-Wallace non-parametric ANOVA, multiple column comparison test using the InStat program (GraphPad Software).

A marginal increase in extramedullary hematopoiesis, especially in the red pulp was seen in spleens of mice from the highest dose group, even in the mice treated for four days. Flow cytometric analysis of the spleens showed a significant increase in the proportion of myeloid size cells in the highest dose group (p=0.01, Student's t test), representing increases in both monocytes and neutrophils. This effect may be related to the increased peripheral blood mononuclear cell percentage, as well as the apparent increase in myeloid precursors in the bone marrow, described above. Moreover, the transgenic mice derived from insertion of the human IL-21 gene had increased extramedullary hematopoiesis in their spleens compared to non-transgenic litter mates.

Several changes were observed in the 50 µg per day dose group compared to the control group that implicate IL-21 in production or development of cells of the myeloid lineage.

Taken together, the observed changes suggest that IL-21 may be useful as a therapeutic protein in immunologic disorders described herein.

Example 2

Preliminary Elimination and Tissue Distribution Study of Purified Recombinant Human IL-21 Protein A. Summary In order to elucidate tissue distribution and elimination patterns of the purified recombinant human IL-21, a preliminary pharmacokinetic study was undertaken. Nine week old male C57Bl/6 mice were given purified recombinant human IL-21 protein labeled with $^{111}$Indium ($^{111}$In) (NEN, Boston, Mass.) by one of three routes. A single bolus injection was given to each mouse by either the intravenous (IV), intraperitoneal (IP), or subcutaneous route (SC). The mice injected by either the subcutaneous or intraperitoneal route were sacrificed at either one or three hours after injection. The mice injected intravenously were sacrificed after either ten minutes or one hour following injection. Blood, plasma and selected tissues were harvested at various timepoints and counted by a gamma counter to estimate the approximate half-life and tissue distribution of the exogenous labeled protein. The tissues that were harvested for counting as well as the intervals of sacrifice were selected based on reports of the distribution of other cytokines labeled with radionuclides.

At sacrifice, tissues harvested for counting of radioactivity included thymus, spleen, kidney, a lobe of liver, a lobe of lung, and urinary bladder. In the group receiving the injection intraperitoneally, gut was also counted to assess incidence of injection into the gut, and in the subcutaneously dosed mice, skin with underlying structures in the area of injection was counted. The cpm for whole liver and lung were calculated from a section that was counted and a percentage of the whole organ weight represented by the section.

After the end of the study the collected tissues, whole blood and plasma were counted on the COBRA II AUTO-GAMMA gamma counter (Packard Instrument Company, Meriden, Conn.). An aliquot of the original labeled dosing solution was also counted at the end of the study with the tissues. This allowed calculation of percent total injected radioactivity for each mouse and simultaneous correction of all counts for radioactive decay. Approximations of remaining blood volume and organ weights indicated that the majority of the counts administered were accounted for, and therefore the percentage of counts per tissue were a reasonable representation of distribution of the counts following labeled IL-21 administration by each route.

B. $^{111}$Indium Labeling of IL-21

Purified recombinant human IL-21 (U.S. Pat. No. 6,307, 024) was conjugated with a 10 fold molar excess of DTPA (Pierce, Rockford, Ill.) by incubating 30 minutes at room temperature in PBS. Unreacted DTPA and hydrolyzates were removed by buffer exchange on a Biomax-5k NMWL (Ultrafree-15, Millipore, Bedford, Mass.). The void volume protein peak was concentrated to 5 mg/ml and an aliquot taken for testing in a bioassay (anti-CD40 stimulation of murine B-cells (Example 10)). Upon confirming that the DTPA-conjugate still had full bioactivity the conjugate was diluted to 0.5 mg/ml with 1M Na Acetate pH6.0. Two mCi of $^{111}$Indium was taken up in 0.5 ml 1M Na Acetate pH6.0 and mixed with the DTPA-human IL-21 for 30 min. at room temperature. Unincorporated $^{111}$Indium was removed during buffer exchange to PBS on a PD-10 column (Pharmacia, Piscataway, N.J.). The radio-labeled material was diluted with unlabeled human IL-21 to give a specific activity of 100 mCi/mg, sterile filtered and stored at 4° C. overnight. One hundred percent of the labeled protein was retained on a Biomax-5k NMWL membrane (Millipore). The labeled $^{111}$In-human IL-21 was administered to mice in the elimination and pharmacokinetic studies. Fifty μg human IL-21 protein labeled with 5 μCi of labeled human IL-21 in 0.1 ml of PBS vehicle was administered to each animal.

C. Results of Preliminary Distribution Study

After one and three hours following administration by all three routes, the highest concentration of $^{111}$In-human IL-21, was found in kidney and the second highest was in urine and urinary bladder, as evinced by these tissues having the highest cpm. The average counts recovered from kidneys were from 3 to 8 times higher than the whole liver counts, depending on the route of injection and the sacrifice timepoint. For example, the average kidney cpm at 60 minutes following IV injection was 4.5 times greater than the average counts calculated for whole liver from the same group. In the group that was sacrificed ten minutes after intravenous administration, the highest cpm was again in kidney, and the second highest accumulation was equivalent in liver, urinary bladder and urine.

D. Preliminary Pharmacokinetic Study

Blood and plasma collections were done at 10, 30 and 60 minutes following injection by all three routes. Following injection by the IV route, a separate set of mice had blood and plasma samples taken at two, five and ten minutes. Another set of mice who received their injections by either the IP or SC route had blood sampled at one, two and three hours. For the treatment groups see Table 4. The short collection times bracket the reported half-life of IL-2 following intravenous injection. The reported T1/2 was in the range of 2.5 to 5.1 minutes. For reference to in vivo administration to IL-2, see Donohue J H and Rosenberg S A *J Immunol,* 130:2203, 1983. The long timepoints were chosen to outline the anticipated elimination phase.

TABLE 4

| Route of injection | Bleed Times(min.) | Sacrifice Time |
| --- | --- | --- |
| Intravenous Group 1 | 2, 5, 10 | 10 min. |
| Intravenous Group 2 | 10, 30, 60 | 60 min. |
| Intraperitoneal Group 1 | 10, 30, 60 | 60 min. |
| Intraperitoneal Group 2 | 60, 120, 180 | 180 min. |
| Subcutaneous Group 1 | 10, 30, 60 | 60 min. |
| Subcutaneous Group 2 | 60, 120, 180 | 180 min. |

Unlabeled IL-2 has been shown to be eliminated from the serum with a half-life of approximately three minutes in mice after IV injection. For reference see Donahue, J H and Rosenburg supra. Following IP and SC injection of similar amounts of IL-2, the duration of persistence of IL-2 activity in serum was prolonged from 2 units/ml for less than 30 minutes following IV injection to greater than 2 units/ml for 2 hours following IP and 6 hours following SC injections. The principle route of clearance of IL-2 appears to be the kidney. IL-21 has been shown to be structurally similar to IL-2, as discussed herein. Preliminary evaluation of the elimination of IL-21 appears to be consistent with the apparent clearance of IL-2 by the kidneys, based on the accumulation of cpm predominantly in the kidneys, followed by the urinary bladder and urine in the present study.

Estimations were made of pharmacokinetic parameters based on non compartmental analysis of the cpm data obtained from the plasma, using the PK analysis program WinNonLin, Version 1.1, (Scientific Consulting Inc., Cary, N.C.). Plasma half-lives of IL-21 were estimated using the predicted terminal elimination rate constants for intravenous, subcutaneous, and intraperitoneal administration of a 50 μg dose. The pharmacokinetic results were estimations due to limited data points in the terminal elimination region of the plasma concentration vs. time profiles. Moreover, the fit of the terminal elimination phase for SC and IP dosing required use of data from timepoints during which absorption of the $^{111}$In-human IL-21 was apparently still occurring. However, estimations of half-lives following intravenous, subcutaneous, and intraperitoneal dosing were 13.6 min., 18.8 min., and 34.3 min., respectively. Since a dosing range was not evaluated it was not apparent whether saturable or active elimination (Michaelis Menten kinetics) was occurring. Therefore, these half-life calculations are estimations.

Estimates of the bioavailability of the labeled protein were made based on the area under the curve (AUC) following subcutaneous or intraperitoneal dosing compared to that of intravenous dosing. The estimated bioavailability following subcutaneous and intraperitoneal injection were 35.8% and 63.9% respectively. Because only one protein dose was studied, the bioavailability was not evaluated as a function of dose. The estimated clearance and volume of distribution (based on the data from the intravenous injection) were 0.48 ml/min. and 6.1 ml, respectively.

Although the data are preliminary, the fate of IL-21 administered IV was similar to that reported for IL-2, another 4-helix bundle cytokine (Donahue, J H and Rosenburg, S A supra.). Like IL-2, IV-administered IL-21 had a plasma half life of only minutes with the main clearance in the kidney. Three hours after injection, the majority of the labeled material extracted from kidney was still retained in a Biomax 5K NMLW membrane (Millipore). Since it has previously been reported that the indium remains associated with protein even during lysosomal degradation (Staud, F. et al., *J. Pharm. Sciences* 88:577-585, 1999) IL-21 is accumulating and may be degraded in the kidney. The current study also showed, as observed with many other proteins, including IL-2 (Donahue, J H and Rosenburg, S A, supra.), that IP and SC administration significantly prolonged the plasma levels of IL-21.

Example 3

Isolation and Expansion of Fresh Human Bone Marrow MNC CD34+ Fraction Using IL-21 for Assessment of NK Activity A. Selection and Isolation of CD34+ Cells from Human Bone Marrow Fresh human bone marrow mononuclear cells (MNC) were prepared to enrich for cells having NK cell activity. Fresh human MNCs were obtained from Poeitic Technologies (Gaithersburg, Md.). 10 ml alpha MEM (JRH, Lenexa, Kans.) containing 10% HIA FBS (Hyclone, Logan, Utah) and the antibiotic 1% PSN (Gibco, BRL, Grand Island, N.Y.) was added to the cell suspension and the cells were passed through a 100 μm sieve. The cells were then counted, pelleted, washed with 10 ml PBS containing 2% FBS, then pelleted again and resuspended in 1 ml PBS containing 2% FBS. Cells having a CD34 cell surface marker (CD34+ cells) were magnetically separated using a Detachabead kit with Dynabeads M-450 CD34 ((Dynal, Oslo, Norway), as per manufacturer's instructions. Both the CD34+ cell and the CD34− cell fractions were further analyzed below.

B. Expansion of CD34+ Cells Using IL-21

A CD34+ cell fraction was plated into four wells in a 24-well plate. 50,000 positively selected cells suspended in 1 ml Alpha MEM (JRH) containing 10% HIA FBS (Hyclone) and 1% PSN (Gibco/BRL), plus the various cytokines described below were plated in each of the 4 wells (1-4). Various reagents were used to test for zalpha11 Ligand-induced expansion of the CD34+ selected bone marrow MNCs: Reagents included human flt3 (R&D, Minneapolis, Minn.); purified human IL-21 (U.S. Pat. No. 6,307,024); human IL-15 (R&D). Reagents were combined as follows at day 0: In well #1, 2 ng/ml human flt3 was added. In well #2, 2 ng/ml human flt3 and 15 ng/ml purified human IL-21 were added. In well #3, 2 ng/ml human flt3 and 20 ng/ml human IL-15 were added. In well #4, 2 ng/ml human flt3, 15 ng/ml purified human IL-21, and 20 ng/ml human IL15 were added. After incubating for 18 days, the suspension cells from each well were pelleted, and then resuspended in 0.5 ml alpha MEM (JRH) containing 10% HIA FBS (Hyclone) and 1% PSN (Gibco/BRL), and counted to assess proliferation of the CD34+ cell fraction. A low level of proliferation was seen in the presence of flt3 alone (control well #1), but the presence of IL-15 or IL-21 in addition to flt3 had not significant effect on the expansion (wells, #2 and #3). However, expansion beyond the flt3 control was evident in well #4 which contained IL-15 and IL-21 in addition to flt3. This result suggested that IL-21 and IL-15 act in synergy to expand the human CD34+ cell population.

All cell populations were then tested for NK activity and subjected to flow cytometry analysis, as shown below (Example 5).

C. Expansion of CD34+ or CD34− Cells Using IL-21 with Delayed Addition of IL-15

Both CD34 positive and negative (CD34−) fractions were plated separately into six 12 well plate wells (1-6). Each of six wells contained 100,000 positively or negatively selected cells in 2 ml alpha MEM containing 10% HIA FBS and PSN, described above. Reagents used were as described above. In well #1, 2 ng/ml human flt3 was added at day 0. In well #2, 2 ng/ml human flt3 was added at day 0, and after 5 days incubation 20 ng/ml human IL-15 was added. In well #3, 2 ng/ml human flt3 and 15 ng/ml human IL-21 were added at day 0. In well #4, 2 ng/ml human flt3 and 15 ng/ml human IL-21 were added at day 0, and after 5 days incubation 20 ng/ml human IL-15 was added. In well #5, 2 ng/ml human flt3 and 20 ng/ml human IL-15 were added at day 0. In well #6, 2 ng/ml human flt3, 15 ng/ml human IL-21, and 20 ng/ml human IL-15 were added at day 0. After incubating for a total of 15 days from the start of the experiment, the cells from each well were harvested and counted.

In the CD34+ population a low level of proliferation was seen in the presence of flt3 alone (control well #1), but the presence of IL-15 or IL-21 added at day 0 in addition to flt3 had no significant effect on the expansion (wells, #3 and #5). Addition of IL-15 after 5 days had some proliferative effect in comparison to the flt3 control (well #2 compared to well #1) and a proliferative effect in the presence of zalpha11 (well #4 compared to well #3). However, the greatest expansion was evident in well #6 which contained IL-15 and IL-21 in addition to flt3 at day 0.

In the CD34− population, no proliferation was seen in the presence of flt3 alone (control well #1), and in fact a decrease in the cell population was evident. The presence of IL-21 added at day 0 in addition to flt3 (well #3) was similar to the flt3 control. The presence of IL-15 added at day 5 increased proliferation effect of the cells in the presence (well #4) or absence (well #2) of IL-21. Again, the greatest expansion was evident in well #6 which contained IL-15 and IL-21 in addition to flt3 at day 0.

All cell populations were then tested for NK activity and subjected to FACS analysis, as shown below (Example 5).

Example 4

Isolation and Expansion of Fresh Mouse Cells Using Human and Mouse IL-21 or Assessment of NK Activity and NK Cell Markers A. Isolation and Expansion of Fresh Mouse Low Density Bone Marrow Cells Using Human and Mouse IL-21

Fresh mouse marrow cells were isolated by clipping both ends of mouse femurs, and flushing two to three milliliters of growth medium (see below) through the inside of the bone into a collection tube. The growth medium was 500 ml RPMI 1640 Medium (JRH Biosciences. Lenexa, Kans.); 5 ml 100× L-glutamine (Gibco BRL. Grand Island, N.Y.); 5 ml 100× Na Pyruvate (Gibco BRL); 5 ml 100× Penicillin, Streptomycin, Neomycin (PSN) (Gibco BRL); and 50 ml heat-inactivated Fetal Bovine Serum (FBS) (Hyclone Laboratories. Logan, Utah). The marrow cells were then broken-up by pipetting the media up and down several times. The cells were then pelleted and washed once with growth medium, and passed through a 70-micron sieve. The low-density mononuclear cells were then isolated by subjecting the marrow cells to a density gradient. Marrow cells in five to eight milliliters of growth medium were carefully pipetted on top of five to eight milliliters of NycoPrep 1.077 Animal (Nycomed. Oslo, Norway) in a centrifuge tube. This gradient was then centrifuged at 600×g for 20 minutes. The low density mononuclear cells were harvested from the interface layer between the Nyco-Prep and the medium. These cells were then diluted to approximately 20 milliliters in growth medium, pelleted and washed. The cells were then plated at approximately 0.5-1.5× $10^6$ cells per milliliter in growth medium in a standard tissue culture flask and incubated at 37° C., 5% $CO_2$ for two hours.

The non-adherent, low density (NA LD) marrow cells were then harvested and plated at 0.5-2.0×$10^5$ cells per milliliter in growth medium plus 2.5 nanograms per milliliter mouse flt3 (R & D Systems. Minneapolis, Minn.) plus 25 to 50 nanograms per milliliter human IL-15 (R & D Systems) with or without 50 to 150 nanograms per milliliter human IL-21; or with or without 0.12 to 10 ng/ml mouse IL-21.

There was no significant expansion without the addition of the human or mouse IL-21. Non-adherent cells were expanded in the cultures containing mouse IL-21 as low as 0.12 ng/ml and in the cultures containing human IL-21 as low as 22 ng/ml. In cultures containing both the human and mouse IL-21, non-adherent cell expansion increased with increasing dose if IL-21, with the mouse ligand saturating response at about 5-10 ng/ml and the human not reaching a saturating response even at the highest dose of 200 ng/ml. Human IL-21 appeared to be approximately 20 to 100 fold less potent on mouse cells as the mouse IL-21. After approximately five to ten days the IL-21 expanded mouse cells were harvested and analyzed by flow cytometry (FACSCalibur; Becton Dickinson, Mansfield, Mass.) to determine what percentage of them were positive for NK cell antigens, where 46% were positive for the PanNK cell marker DX5 (Pharmingen).

B. Isolation and Expansion of Fresh Lineage Depleted Mouse Marrow Cells

Fresh mouse lineage depleted (lin−) marrow cells were isolated from fresh mouse marrow cells by first incubating the cells with the following antibodies: TER119, Gr-1, B220, MAC-1, CD3e and I-Ab (Pharmingen. San Diego, Calif.). The lin+ cells were then removed with Dynabeads M-450 sheep anti-rat IgG (Dynal, Lake Success, N.Y.) as per manufacturer's instructions.

The negatively selected lin− marrow cells were then plated as above in growth medium plus either 2.5 ng/mL flt3 (R&D Systems) and 25 ng/mL IL-15 (R&D Systems); or flt3, IL-15 and mouse IL-21, 2 to 5% BHK mouse IL-21 conditioned medium. After six days of growth, the cultures were harvested, counted and submitted to an NK cell activity assay (Example 5). Cells grown with mouse IL-21 were approximately two to three times more effective at lysing NK cell target cells (YAC-1 cells) as the cells grown without IL-21.

C. Isolation and Expansion of CD4− CD8− (Double Negative or DN) Thymocytes

Fresh mouse thymocytes were isolated by chopping and sieving thymuses from three to eight week old mice. CD4− CD8− (DN) cells were then negatively selected by incubating the thymocytes with anti-CD4 and anti-CD8 antibodies (PharMingen), then removing the CD4+ CD8+ cells with Dynabeads M-450 sheep anti-rat IgG (Dynal) as per manufacturer's instructions.

The DN mouse thymocytes were then grown in growth medium plus 2.5 ng/mL flt3 (R&D Systems), 25 ng/mL IL-15 (R&D Systems) and 10 ng/mL IL-7 (R&D Systems) with or without mouse IL-21 as above. Six days later the cells were harvested, counted, analyzed by flow cytometry as described above, and also submitted to an NK cell activity assay (Example 5).

The culture grown with mouse IL-21 yielded approximately 480,000 cells while the culture without IL-21 yielded only approximately 160,000 cells. The culture grown with mouse IL-21 was found to be approximately 16.2% positive for the NK cell antigen Pan NK, DX5 (PharMingen). The culture grown without IL-21 was 14.6% positive for DX5. The cells grown with IL-21 lysed NK cell target cells, YAC-1, approximately two times better than the cells grown without IL-21. The expanded cells did not lyse significantly a negative control target cell line, EL4. These results suggested that IL-21 selectively expands lytic NK cells.

Example 5

Activity of Human and Mouse IL-21 Expanded Cells and Mature Murine NK Cells in NK Cell Cytotoxicity Assays A. NK Cell Assay NK cell-mediated target cytolysis was examined by a standard $^{51}$Cr-release assay. Target cells (K562 cells (ATCC No. CCL-243) in human assays, and YAC-1 cells (ATCC No. TIB-160) in mouse assays) lack expression of major histocompatibility complex (MHC) molecules, rendering them susceptible to NK cell-mediated lysis. A negative control target cell line in mouse assays is the MHC$^+$ thymoma EL4 (ATCC No. TIB-39). We grew K562, EL4, and YAC-1 cells in RP10 medium (standard RPMI 1640 (Gibco/BRL, Grand Island, N.Y.) supplemented with 10% FBS (Hyclone, Logan, Utah), as well as 4 mM glutamine (Gibco/BRL), 100 I.U./ml penicillin+100 MCG/ml streptomycin (Gibco/BRL), 50 μM β-mercaptoethanol (Gibco/BRL) and 10 mM HEPES buffer (Gibco/BRL). On the day of assay, 1-2×$10^6$ target cells were harvested and resuspended at 2.5-5×$10^6$ cells/ml in RP10 medium. We added 50-100 μl of 5 mCi/ml $^{51}$Cr-sodium chromate (NEN, Boston, Mass.) directly to the cells and incubated them for 1 hour at 37° C., then washed them twice with 12 ml of PBS and resuspended them in 2 ml of RP10 medium. After counting the cells on a hemacytometer, the target cells were diluted to 0.5-1×10$^5$ cells/ml and 100 µl (0.5-1×10$^4$ cells) were mixed with effector cells as described below.

In human assays, effector cells were prepared from selected and expanded human CD34$^+$ BM cells which were harvested, washed, counted, mixed at various concentrations with $^{51}$Cr-labeled target cells in 96-well round bottomed plates, and incubated for 4 hours at 37° C. After co-incubation of effector cells and the labeled target cells, half of the supernatant from each well was collected and counted in a gamma counter for 1 min/sample. The percentage of specific $^{51}$Cr release was calculated from the formula 100×(X−Y)/(Z−Y), where X is $^{51}$Cr release in the presence of effector cells, Y is the spontaneous release in the absence of effectors, and Z is the total $^{51}$Cr release from target cells incubated with 0.5% Triton X-100. Data were plotted as the % specific lysis versus the effector-to-target ratio in each well.

B. Activity of Human IL-21 Expanded Cells

Isolated CD34$^+$ human HPCs cultured with flt3+/−IL-21 and flt3+IL-15+/−IL-21 (Example 5), were harvested the cells on day 15 to assess their capacity to lyse MHC$^-$ K562 cells in a standard $^{51}$Cr-release assay as described above, and to analyze their surface phenotype by flow cytometry. As expected from previous reports (Mrozek, E et al., Blood 87:2632-2640, 1996; and Yu, H et al., Blood 92:3647-3657, 1998), simultaneous addition of IL-15 and flt3L did induce the outgrowth of a small population of CD56$^+$ cells. Interestingly, although BM cells cultured simultaneously with IL-21 and flt3L did not expand significantly, there was a significant increase in total cell numbers in cultures containing a combination of flt3L, IL-21 and IL-15 (see, Example 3).

For an assessment of the surface phenotype of these human BM cultures, we stained small aliquots of the cells for 3-color flow cytometric analysis with anti-CD3-FITC, anti-CD56-PE and anti-CD16-CyChrome mAbs (all from PharMingen, San Diego, Calif.) and analyzed them on a FACSCalibur using CellQuest software (Becton Dickinson, Mountain View, Calif.). This flow cytometric analysis confirmed that the cells growing out of these cultures were differentiated NK cells, as they were large and granular and expressed both CD56 and CD16, and were CD3$^-$ (Lanier, L L Annu. Rev. Immunol. 16:359-393, 1998). Furthermore, these cells exhibited significantly higher effector function than those cells grown with IL-15 and flt3. More specifically, cells grown in all three cytokines lysed more than 40% of the K562 targets at an effector-to-target ratio (E:T) of 1.5, whereas cells grown in IL-15+flt3L lysed fewer than 5% of the targets at an E:T of 2. These data demonstrate that, in combination with IL-15, IL-21 stimulates the differentiation of NK cells from CD34$^+$ BM cells.

C. Activity of Mouse IL-21 Expanded Cells

To test the effects of IL-21 on murine hematopoietic progenitor cells, purified Lineage-negative (Lin−) bone marrow cells from C57Bl/6 mice were expanded in flt3+IL-15+/−IL-21, as described in Example 4B. On day 6 of culture, the cells ("effectors") were harvested and counted, then resuspended in 0.4 ml of RP10 medium (Example 5A). Two aliquots (0.15 ml each) of each sample expanded with or without IL-21 (Example 5A) were diluted serially 3-fold in duplicate in 96-well round bottomed plates, for a total of 6 wells of 100 µl each. The remaining 100 µl of cells were stained for NK cell surface markers with FITC-anti-2B4 and PE-anti-DX5 mAbs (PharMingen) and analyzed by flow cytometry. Each group of cells exposed to flt3+IL-15 with or without the presence of IL-21 had similar fractions of 2B4+DX5+ cells, ranging from 65-75% positive for both NK markers.

For the NK lysis assay, target cells (YAC-1 and EL4) were labeled with $^{51}$Cr as described above. After counting the target cells on a hemacytometer, the target cells were diluted to 0.5-1×10$^5$ cells/ml and 100 µl of YAC-1 or EL4 (0.5-1×10$^4$ cells) were mixed with 100 µl effector cells and incubated for 4 hours at 37° C. Specific lysis was determined for each well as described above.

We found that cells grown in the presence of flt3+IL-15+IL-21 exhibited enhanced lytic activity (roughly 2-fold) against the YAC-1 targets (but did not kill the MHC$^+$ control cell line EL4). At an effector-to-target ratio (E:T) of 5, NK cells generated in the presence of all 3 cytokines (IL-21+flt3+IL-15) lysed 12% of the YAC-1 cells, whereas those NK cells expanded with flt3+IL-15 lysed 6% of the YAC-1 targets. Subsequent experiments confirmed this trend.

In a second approach to determine the biological activity of IL-21 on murine NK cells, we isolated immature CD4$^-$CD8$^-$ ("double negative", DN) mouse thymocytes as described in Example 6C and cultured them with IL-15+flt3+IL-7 or IL-15+flt3+IL-2, with or without IL-21. On day 6 of culture, the cells were harvested and assayed for NK lytic activity on YAC-1 and EL4 cells as described above. We found that cells cultured in the presence of IL-21 had the greatest lytic activity in this assay, with enhanced lytic activity over those cells cultured in the presence of the other cytokines. Specifically, DN thymocytes grown with IL-15+flt3+IL-7 killed 18% of the YAC-1 cells at E:T of 24 while cells grown in the presence of IL-15+flt3+IL-7 plus IL-21 killed 48% of the targets at the same E:T. DN thymocytes grown in IL-15+flt3+IL-2 killed 15% of the YAC-1 targets at an E:T of 6, whereas cells grown with these 3 cytokines and IL-21 killed 35% of the YAC-1 cells at an E:T of 9. Flow cytometry was performed on the cultured cells one day before the NK lysis assay. As was true for the bone marrow cultures, despite the proliferative effect of IL-21 (cell numbers increase approximately 2-fold when IL-21 is added), it did not significantly enhance the fraction of DX5$^+$ cells (17-20% of total cells in the cultures with IL-7, and 35-46% of total in cultures with IL-2). These data imply that IL-21, in combination with IL-15 and flt3, enhances the lytic activity of NK cells generated from murine bone marrow or thymus.

D. Activity of Mouse IL-21 on Mature Murine NK Cells

In order to test the effects of mouse IL-21 on mature NK cells, we isolated spleens from four 5-week old C57Bl/6 mice (Jackson Laboratories, Bar Harbor, Me.) and mashed them with frosted-end glass slides to create a cell suspension. Red blood cells were removed by hypotonic lysis as follows: cells were pelleted and the supernatant removed by aspiration. We disrupted the pellet with gentle vortexing, then added 900 µl of sterile water while shaking, followed quickly (less than 5 sec later) by 100 µl of 10×HBSS (Gibco/BRL). The cells were then resuspended in 10 ml of 1×HBSS and debris was removed by passing the cells over a nylon mesh-lined cell strainer (Falcon). These RBC-depleted spleen cells were then pelleted and resuspended in MACS buffer (PBS+1% BSA+2 mM EDTA) and counted. We stained 300×10$^6$ of the cells with anti-DX5-coated magnetic beads (Miltenyi Biotec) and positively selected DX5$^+$ NK cells over a MACS VS+ separation column, according to the manufacturer's instructions, leading to the recovery of 8.4×10$^6$ DX5$^+$ cells and 251×10$^6$ DX5$^-$ cells. Each of these groups of cells were cultured in 24-well plates (0.67×10$^6$ cells/well, 2 wells per treatment condition) in RP10 medium (Example 7A) alone or with 1) 30 ng/ml mouse zalpha11 Ligand, 2) 30 ng/ml recombinant mouse IL-2 (R&D Systems, Inc., Minneapolis, Minn.), 3) 30 ng/ml recombinant human IL-15 (R&D), 4) 30 ng/ml each of mouse IL-21 and hIL-15, or 5) 30 ng/ml each of mIL-2 and hIL-15. The cells were harvested after 21 hours, washed, and resuspended in RP10 medium and counted. The cells were then assayed for their ability to lyse $^{51}$Cr-labeled YAC-1 or EL4 targets cells, as described in Example 5A.

In general, there was little NK activity from the DX5$^-$ (non-NK cells) groups, but the DX5$^-$ cells cultured with IL-21 and hIL-15 did lyse 25% of the YAC-1 target cells at an E:T of 82. By comparison, DX5$^-$ cells cultured with hIL-15 alone lysed 14% of the YAC-1 targets at an E:T of 110. This suggests that IL-21 and IL-15 are acting together on the residual NK1.1$^+$ NK cells in this cell preparation. As for the DX5$^+$ cell preparation, treatment with mouse IL-21 alone did not significantly increase their effector function (their lysis of YAC-1 cells was similar to the untreated group). As expected, both IL-2 and IL-15 significantly improved NK activity. The highest level of lysis, however, was detected in the group treated with IL-21 and hIL-15 (65% lysis of YAC-1 cells at an E:T of 3.3, vs. 45% lysis at an E:T of 4 for the hIL-15 treatment group). Taken together, these results suggest that although IL-21 alone may not increase NK cell lysis activity, it does enhance NK lysis activity of mature NK cells, when administered with IL-15.

Example 6

IL-21 Proliferation of Human and Mouse T-Cells in a T-Cell Proliferation Assay

A. Murine IL-21 Proliferation of Mouse T-Cells

T cells from C57Bl/6 mice (Jackson Laboratories, Bar Harbor, Me.) were isolated from pooled splenocytes and lymphocytes from axillary, brachial, inguinal, cervical, and mesenteric lymph nodes (LNs). Spleens were mashed with frosted-end glass slides to create a cell suspension. LNs were teased apart with forceps and passed through a cell strainer to remove debris. Pooled splenocytes and LN cells were separated into CD8$^+$ and CD4$^+$ subsets using two successive MACS magnetic separation columns, according to the manufacturer's instructions (Miltenyi Biotec, Auburn, Calif.). Whole thymocytes were collected from the same mice.

Cells were cultured at 3×10$^5$ cells/well (thymocytes) or 10$^5$ cells/well (mature T cells) with increasing concentrations of purified murine IL-21 (0-30 ng/ml) (U.S. Pat. No. 6,307,024) in 96-well flat bottomed plates pre-coated overnight at 4° C. with various concentrations of anti-CD3 mAb 2C11 (PharMingen) for 3 days at 37° C. The anti-CD3 antibody served to activate the murine T-cells through the T-cell receptor. Each well was pulsed with 1 µCi $^3$H-thymidine on day 2 and plates were harvested and counted 16 hours later to assess proliferation.

When we tested IL-21 in T cell proliferation assays, we found that it co-stimulated anti-CD3-activated murine thymocytes, leading to an accelerated outgrowth of CD8$^+$CD4$^-$ cells (the majority of the thymocytes cultured with anti-CD3+ IL-21 were CD8$^+$CD4$^-$ by day 3 of culture, while cells cultured with anti-CD3 alone did not significantly skew to this phenotype until day 5). We did not observe significant levels of proliferation of thymocytes to IL-21 in the absence of anti-CD3.

Interestingly, when we assayed mature peripheral murine T cells for their ability to respond to IL-21+anti-CD3, we found that only the CD8$^+$, but not the CD4$^+$ subset, responded in a dose-dependent manner to IL-21. We also observed weak but reproducible proliferation of CD8$^+$ cells (but not CD4$^+$ cells) in response to IL-21 alone.

B. Human IL-21 Proliferation of Human T-Cells

In an initial experiment, human CD4+ and CD8+ T cells were isolated from PBMC as described in Example 9 (below) Cells were cultured at about 10$^5$ cells/well with increasing concentrations of purified human IL-21 (0-50 ng/ml) (U.S. Pat. No. 6,307,024) in 96-well flat bottomed plates pre-coated overnight at 4° C. with various concentrations of anti-human CD3 mAb UCHT1 (PharMingen) for 3 days at 37° C. Each well was pulsed with 1 µCi $^3$H-thymidine on day 2 and plates were harvested and counted 16 hours later. Unlike our results with mouse T cells, our preliminary data suggests that human IL-21 co-stimulates CD4+, but not CD8+, human T cells in a dose-dependent fashion.

In other experiments, mature murine CD4+ and CD8+ T cells were enriched from pooled C57Bl/6 spleen and LN cells by depletion of CD19$^+$ B cells using a magnetic bead column. The resulting cell populations were assayed for proliferation to plate-bound anti-mouse CD3ε mAb in the absence or presence of increasing concentrations of murine IL-21, as indicated. Data shown are representative of results from 4 experiments.

T cells from C57Bl/6 mice were isolated from pooled splenocytes and lymphocytes from auxiliary, brachial, inguinal, cervical, and mesenteric LNs. Spleens were mashed with frosted-end glass slides to create a cell suspension. LNs were teased apart with forceps and passed through a cell strainer to remove debris. Pooled splenocytes and LN cells were separated into CD8$^+$ and CD4$^+$ subsets using two successive MACS magnetic separation columns, according to the manufacturer's instructions (Miltenyi Biotec, Sunnyvale, Calif.). Cells were cultured at 10$^5$/well with increasing concentrations of murine IL-21 (0-30 ng/ml) in 96-well flat bottomed plates pre-coated overnight at 4° C. with various concentrations of anti-CD3ε mAb 2C11 (PharMingen) for 3 days at 37° C. Each well was pulsed with 1 µCi $^3$H-thymidine on day 2 and plates were harvested and counted 16 hours later.

Table 5 illustrates that mIL-21 co-stimulates the proliferation of murine CD8+ T cells. Values represent the CPM incorporated of $^3$H-thymidine (average+/−standard deviation of triplicate wells).

TABLE 5

|  | ng/ml mIL-21 | Anti-CD3 mAb (ug/ml) | | | | |
|---|---|---|---|---|---|---|
|  |  | 0 | 0.11 | 0.33 | 1.0 | 3.0 |
| CD4+ | 0 | 405 +/− 101 | 67895 +/− 18752 | 141175 +/− 6733 | 202251 +/− 35571 | 246626 +/− 45106 |
|  | 1.2 | 247 +/− 86 | 80872 +/− 23598 | 126487 +/− 7472 | 178863 +/− 33583 | 205861 +/− 14675 |
|  | 6 | 302 +/− 106 | 75192 +/− 5323 | 102005 +/− 20059 | 191598 +/− 15881 | 218718 +/− 12142 |
|  | 30 | 364 +/− 126 | 86164 +/− 8065 | 141065 +/− 4921 | 186089 +/− 17585 | 266650 +/− 39839 |
| CD8+ | 0 | 168 +/− 47 | 40198 +/− 4557 | 70272 +/− 4141 | 84771 +/− 9450 | 97869 +/− 3368 |
|  | 1.2 | 268 +/− 117 | 50095 +/− 3959 | 84319 +/− 6373 | 105176 +/− 10828 | 113394 +/− 3657 |
|  | 6 | 323 +/− 159 | 78113 +/− 6967 | 108461 +/− 2175 | 132301 +/− 13386 | 178551 +/− 16373 |
|  | 30 | 2007 +/− 470 | 132238 +/− 1915 | 182485 +/− 4991 | 272229 +/− 9325 | 330434 +/− 47185 |

Example 7

IL-21 Effects on Serum Cytokines and Vascular Leak

A. Analysis of IL-21 on Serum Cytokines

IL-2 therapy is effective in the treatment of certain cancers. However, the use of IL-2 as a therapeutic agent has been limited by its toxic effects, namely vascular leak syndrome (VLS). IL-2 induced VLS is characterized by infiltration of lymphocytes, monocytes and neutrophils into the lung causing endothelial damage in the lung eventually leading to vascular leak (reviewed in Lentsch A B et al, *Cancer Immunol. Immunother.*, 47:243, 1999). VLS in mice can be induced with administration of repeated high doses of IL-2 and measuring vascular leak by Evan's Blue uptake by the lung. Other parameters that have been shown to be characteristic of VLS in mice include increased serum levels of TNFα and IFNγ (Anderson J A et al, *J. Clin. Invest.* 97:1952, 1996) as well as increased numbers of activated T, NK and monocytes in various organs. Blocking of TNFα with a soluble TNFR-Fc molecule inhibited lung infiltration by lymphocytes and therefore lung injury (Dubinett S M et al, *Cell. Immunol.* 157:170, 1994). The aim was to compare the ability of IL-2 and IL-21 to induce VLS in mice and to measure the different parameters indicative of VLS (Evan's Blue uptake, serum cytokine analysis, spleen cellular phenotype).

Mice (female, C57Bl6, 11 week old; Charles River Labs, Kingston, N.Y.) were divided into five groups. All groups contained 10 mice per group. Groups are as follows: Group I or Vehicle group received Phosphate Buffered Saline (PBS); Group II and III received IL-2 0.6 or 1.8 million IU/injection respectively; Group IV and V received mouse IL-21 (U.S. Pat. No. 6,307,024) or 100 μg/injection respectively. The study consisted of 4 days, body weight was measured daily and animals received 7 intraperitoneal injection of test substance over the 4-day period. Animals received two daily injections on day 1-3 and on the fourth day received a single morning injection. Two hours post final injection animals received a tail vein injection of 1% Evan's blue (0.2 ml). Two hours post Evan's blue injection mice where anesthetized with Isoflurane and blood was drawn was serum cytokine analysis. Following blood draw animals where transcardial perfused with heparinized saline (25 Uhep/ml saline). Following perfusion spleen was removed and weighed, liver and lung where removed and placed into 10 mls of formamide for 24 hr incubation at room temperature. Following 24 hr incubation vascular leakage was quantitated by Evan's blue extravasation via measurement of the absorbance of the supernatant at 650 nm using a spectrophotometer.

Mice were bled and serum separated using a standard serum separator tube. 25 μl of sera from each animal was used in a Becton Dickenson (BD) Cytokine Bead Array (Mouse Th1/Th2 CBA Kit) assay. The assay was done as per the manufacturer's protocol. Briefly, 25 μl of serum was incubated with 25 μl bead mix (IL-2, IL-4, IL-5, TNFα and IFNγ) and 25 μl PE-detection reagent for two hours at room temperature in the dark. A set of cytokine standards at dilutions ranging from 0-5000 pg/ml was also set up with beads as per the manufacturer's instructions. The incubated beads were washed once in wash buffer and data acquired using a BD FACScan as per instructions outlined in the Kit. The data was analyzed using the BD Cytometric Bead Array Software (BD Biosciences, San Diego, Calif.).

Serum cytokine analysis using the CBA cytokine kit (Becton Dickenson, San Diego, Calif.) showed no increases in levels of IL-2, IL-4, IL-5, IFNγ or TNFα in the PBS control treated groups. There was a dose dependent increase in the levels of IL-5, IFNγ and TNFα in sera from IL-2 treated mice. There was no increase in the levels of the 5 measured cytokines in the serum of mice treated with IL-21. The cytokine levels in the highest dose of IL-21 mirrored that of the PBS treated animals. This shows that unlike IL-2 treatment that leads to increase in serum levels of the inflammatory cytokines IL-5, TNFα and IFNγ, treatment with IL-21 does not have any effect on these inflammatory cytokines.

The results from a representative experiment is given in Table 5. All concentrations are expressed in pg/ml were an average of 4 animals/group.

TABLE 6

|  | TNFα | IFNγ | IL5 | IL4 | IL2 |
|---|---|---|---|---|---|
| PBS | 2.4 | 0.0 | 2.9 | 2.2 | 1.3 |
| IL2 0.6 millU | 22.9 | 21.6 | 1095.0 | 2.5 | 2.0 |
| IL2 1.8 millU | 69.1 | 185.1 | 1132.9 | 2.0 | 1.9 |
| IL2 3.6 millU | 78.9 | 195.6 | 651.3 | 1.8 | 2.1 |
| IL-21 33 μg | 2.1 | 1.6 | 2.7 | 1.7 | 1.6 |
| IL-21 100 μg | 3.1 | 0.0 | 4.0 | 0.0 | 1.1 |
| IL-21 200 μg | 7.3 | 1.9 | 4.0 | 2.6 | 1.9 |

As shown in Table 5 above, treatment of mice with IL-2 resulted in a dramatic increase in serum inflammatory cytokines, namely IL-5, IFNγ and TNFα. Treatment of mice with IL-21 did not show any increase in cytokine levels above PBS treated mice. These results show that even at the highest doses, IL-21 does not upregulate inflammatory cytokines and it's effect on cells in vivo is different from IL-2.

Treatment of mice with repeated high dose IL-2 resulted in increased serum levels of IL-5, IFNγ and TNFα. These proinflammatory cytokines have been shown to play a role in VLS associated with IL-2 toxicity. Blocking TNFα resulted in decreased lymphocyte infiltration into the lungs and decreased lung injury associated with IL-2 toxicity (Dubinett S M et al, 1994, Cell. Immunol. 157:170). IL-21 treatment did not have any effects on serum IL-5, TNFα or IFNγ levels. This suggests that IL-21 acts different from IL-2 in vivo and that the lack of pro-inflammatory cytokines in sera of IL-21 treated mice might indicate lesser toxicity of IL-21 compared to IL-2.

B. Analysis of IL-21 on Vascular Leak—Immunophenotyping of Splenic Cells

IL-2 induced vascular leak syndrome (VLS) involves organ damage that occurs at the level of postcapillary endothelium. However, this damage occurs secondary to two distinct pathological processes: the development of VLS, and transendothelial migration of lymphocytes. Acute organ injury is mediated by infiltrating neutrophils while chronic organ injury is mediated by infiltration monocytes and lymphocytes (reviewed in Lentsch A B et al, supra.). In mice, depletion of cells with surface phenotypes characteristic of LAK or NK cells ameliorates organ damage (Anderson T D et al, *Lab. Invest.* 59:598, 1988; Gately, M K et al. *J. Immunol.*, 141:189, 1988). Increased numbers of NK cells and monocytes is therefore a marker for IL-2 mediated cellular effects of VLS. In addition, IL-2 directly upregulates the expression of adhesion molecules (i.e LFA-1, VLA-4 and ICAM-1) on lymphocytes and monocytes (Anderson J A et al, supra.). This increase is thought to enable cells to bind activated endothelial cells and help in transmigration of cells to the tissue. Increased expression of these molecules is considered another marker of IL-2 induced cellular activation during VLS. The aim of this study was to study splenic cells from IL-2 and IL-21 treated mice under a VLS protocol and compare the effects of the two cytokines to mediate cellular effects associated with VLS.

Groups of age and sex matched C57BL/6 mice treated and described above were analysed. On d4, mice were sacrificed and phenotype of splenic cell populations studied by standard flow cytometry. Splenic weight and cellularity were dramatically increased in IL-2 treated mice compared to PBS treated mice. IL-21 treated mice had a slight increase in splenic weights (at the higher doses) but no significant increase in splenic cellularity compared to the PBS treated groups. Cell population analysis showed a significant increase in the percentage and numbers of NK, NKT and monocytes in IL-2 treated mice but not in the IL-21 treated mice. Furthermore, there was a dose dependent dramatic increase in LFA-1 expressing cells in the IL-2 treated groups compared to PBS controls. IL-21 treatment had no effect on LFA-1 expression on splenic cells.

Spleens were isolated from mice from the various groups. Red blood cells were lysed by incubating cells for 4 minutes in ACK lysis buffer (0.15M NH4Cl, 1 mM KHCO3, 0.1 mM EDTA) followed by neutralization in RPMI-10 media (RPMI with 10% FBS). The expression of cell surface markers was analyzed by standard three color flow cytometry. All antibodies were obtained from BD Pharmingen (San Diego, Calif.). Fluorescin-isothiocyanate (FITC) conjugated CD11a (LFA-1), CD49d (VLA-4, a chain), Gr-I FITC, phycoerythrin (PE) conjugated CD4, NK1.1, CD11b and CyC-conjugated CD8, CD3 and B220 were used to stain cells. 1-3×10$^6$ cells were used for individual stains. Non-specific binding was blocked by incubating cells in blocking buffer (PBS, 10% FBS, 20 ug/ml 2.4G2). After blocking, cells were incubated with primary antibodies for 20 minutes. Unless specified otherwise, all mAbs were used at 1 ug/stain in a volume of 100 ul. Cells were washed once in 1×PBS and resuspended in PBS before being acquired using the FACScan or FACSCalibur instruments (BD Biosciences, San Diego, Calif.). Data was analyzed using the Cellquest Software (BD Biosciences).

IL-2 treated mice had significantly increased spleen weights compared to PBS treated groups (Table 6, below) IL-21 treated mice had significant increase in spleen weight over controls. However, the increases in IL-21 treated groups were significantly less than in the IL-2 treated groups (p=0.0002). The increase in spleen weights in both groups was dose dependent. Table 6 below shows the treatment groups; the average splenic weights were shown in mg, and n=4.

TABLE 7

| | Total spleen weight (mg) | Stdev | p value (vs PBS) |
|---|---|---|---|
| PBS | 63.5 | 9.7 | 0 |
| IL-2 (0.6) | 177.5 | 17.8 | <0.0001 |

TABLE 7-continued

| | Total spleen weight (mg) | Stdev | p value (vs PBS) |
|---|---|---|---|
| IL-2 (1.8) | 204.25 | 10 | <0.0001 |
| IL-2 (3.6) | 231.2 | 9.6 | <0.0001 |
| IL-21(33) | 92.8 | 6 | 0.0022 |
| IL-21(100) | 117.6 | 19.3 | 0.0024 |
| IL-21(200) | 125.85 | 33 | 0.0111 |

Average Splenic cellularity data is shown in Table 7, below (n=4). Higher dose IL-2 treatment increased splenic cellularity significantly over control PBS treated groups. IL-21 treated groups did not show significant increase in splenic cellularity compared to PBS groups.

TABLE 8

| | Total cells (×10e6) | Stdev | p value (vs PBS) |
|---|---|---|---|
| PBS | 48 | 16.4 | 0 |
| IL-2 (0.6) | 57.1 | 11.8 | 0.4014 |
| IL-2 (1.8) | 100.4 | 21.6 | <.0083 |
| IL-2 (3.6) | 101.8 | 4.25 | <.0007 |
| IL-21(33) | 58.8 | 13.5 | 0.3463 |
| IL-21(100) | 48 | 7.83 | 0.9769 |
| IL-21(200) | 53.8 | 22.5 | 0.6917 |

IL-2 induced VLS is characterized by increased numbers of NK cells, monocytes and cells expressing the adhesion marker LFA-1 (reviewed in Lentsch A B et al, supra.). The above data using IL-2 reproduces published reports on the increase of NK cells, monocytes and LFA-1+ cells. IL-2 treated mice show all signs of VLS compared to controls. In contrast, IL-21 treated mice, although having an increased uptake of Evan's Blue, show no increase in serum pro-inflammatory cytokines, or increase in LFA-1+ cells or NK cells. Furthermore, although IL-21 treated mice do show increased numbers of monocytes, the increase is less than what is seen with IL-2 treated animals, suggesting that IL-2 mediated effects are more severe than IL-21 mediated effects. Taking together the splenic cellularity data and the serum cytokine data, IL-21 does not induce a comparable inflammatory response as IL-2. All parameters analyzed would indicate that IL-21 induces minor if any inflammatory response when administered in a VLS protocol in similar doses to IL-2 (weight/weight).

In addition, as shown in Table 8 and Table 9, below, flow cytometry analysis of spleen cells from mice revealed that IL-2 treated mice had a dose dependent increase in the % and numbers of splenic NK/T cells (NK1.1+CD3+), NK cells (NK1.1+CD3−), macrophages (CD11b+) and LFA-1+ cells (TABLE III and IV). IL-21 treated mice had no increase in NK/T cells, NK cells or LFA-1+ cells. There was an increase in the % and numbers of macrophages and granulocytes (data not shown) in IL-21 treated group compared to the control PBS treated groups. This increase was similar or less than the increase in IL-2 treated mice.

TABLE 9

Average % of lineage cells in spleen (n = 4)

| | % NK/T | % NK | % macrophages | % B | % CD4 T | % CD8 T | % LFA-1+ |
|---|---|---|---|---|---|---|---|
| PBS | 0.7225 | 3.1925 | 6.625 | 50.025 | 21.975 | 14.275 | 11.1775 |
| IL-2 (0.6) | 4.34 | 9.3375 | 12.525 | 43.9 | 17.65 | 10.15 | 29.26 |
| IL-2 (1.8) | 3.2 | 13.9 | 14.525 | 43.75 | 15.55 | 11.55 | 34.825 |
| IL-2 (3.6) | 3.075 | 14.3 | 11.875 | 42.8 | 14.875 | 17.325 | 44.05 |
| IL-21(33) | 0.615 | 2.9875 | 7.825 | 53.65 | 17.925 | 10.95 | 8.4375 |

TABLE 9-continued

Average % of lineage cells in spleen (n = 4)

|  | % NK/T | % NK | % macrophages | % B | % CD4 T | % CD8 T | % LFA-1+ |
|---|---|---|---|---|---|---|---|
| IL-21(100) | 0.63 | 2.76 | 11.375 | 48.325 | 17.825 | 11.275 | 13.35 |
| IL-21(200) | 1.025 | 3.4325 | 16.175 | 45.125 | 17.225 | 12.15 | 15.7 |

TABLE 10

Splenic cell numbers ($\times 10^6$ cells, n = 4)

|  | NKT | NK | CD11b | B220 | Cd4 | Cd8 | LFA-1 | Gr-1 |
|---|---|---|---|---|---|---|---|---|
| PBS | 0.33 | 1.54 | 3.19 | 24.34 | 10.19 | 6.58 | 5.41 | 1.11 |
| IL-2 (0.6) | 2.34 | 5.33 | 7.04 | 25.23 | 10.16 | 5.77 | 16.60 | 2.82 |
| IL-2 (1.8) | 3.08 | 14.29 | 14.16 | 43.63 | 15.57 | 11.62 | 35.11 | 7.65 |
| IL-2 (3.6) | 3.15 | 14.59 | 12.08 | 43.53 | 15.13 | 17.64 | 44.83 | 4.76 |
| IL-21(33) | 0.37 | 1.77 | 4.67 | 31.50 | 10.47 | 6.32 | 5.05 | 1.05 |
| IL-21(100) | 0.30 | 1.33 | 5.35 | 23.16 | 8.55 | 5.40 | 6.35 | 1.54 |
| IL-21(200) | 0.56 | 1.86 | 8.46 | 23.85 | 9.20 | 6.39 | 8.43 | 3.20 |

In addition, additional endpoints were measured between groups. The following endpoints where compared: Body weight, spleen weight, vascular leakage in lung and liver, and serum cytokines. No significant difference in body weights was observed between groups. As discussed above, animals treated with both doses of IL-2, Group II and III, had significantly heavier spleen weights as compared to IL-21 and PBS control treated animals (p<0.0001). Animals treated with both doses of IL-21 treated animals, Group IV and V, had significantly heavier spleen weights as compared to PBS control animals (p<0.007 Group IV and p<0.0001 Group V).

Vascular leakage was also measured in both lung and liver. In lung, both groups of IL-2 treated animals, Group II and III, had a significant increase in vascular leakage (p<0.0001) as compared to PBS control animals. Only Group III, the high dose of IL-2 had a significant increase in vascular leakage as compared to both low dose and high dose IL-21 (p<0.0001 and p<0.0065) respectively. Only the highest dose of IL-21, Group V, had a significant increase in vascular leakage as compared to PBS treated animals (p<0.0001). However, the amount of vascular leak was significantly lower than all of the IL-2 treated animals. In liver, both the low and high dose of IL-2 treated animals had a significant increase in vascular leakage (p<0.0016 and p<0.0001 respectively) as compared to PBS treated animals. Animals treated with the high dose of IL-2 had a significant increase in vascular leakage as compared to both low and high dose IL-21 treated animals (p<0.0002 and p<0.0001 respectively). Only the low dose IL-21 treated animals had a significant increase in vascular leakage as compared to PBS treated animals (p<0.0397).

Example 8

Activity of Mouse IL-21-Treated Alloreactive Murine CTL (Cytotoxicity Assays)

A. CTL Assay

CTL (cytotoxic T lymphocyte)-mediated target cytolysis was examined by a standard $^{51}$Cr-release assay. Alloreactive ($H-2^b$ anti-$H-2^d$) CTL were generated in a mixed lymphocyte culture with C57Bl/6 splenocytes ($H-2^b$) with 3000 rad-irradiated Balb/c splenocytes ($H-2^d$). After 7 days, the CTL were re-stimulated with irradiated Balb/c splenocytes (and no additional cytokines). After an additional 7 days, CTL were re-stimulated for 5 days in the presence of supernatants collected from conA-activated rat splenocytes (a crude source of cytokines known to support CTL growth), 10 ng/ml recombinant mouse IL-2 (R&D Systems, Inc, Minneapolis, Minn.), recombinant human IL-15 (R&D Systems), mouse IL-21, or a combination of IL-15 and IL-21 (5 ng/ml each). After 5 days, the CTL were assayed for their capacity to lyse $^{51}$Cr-labeled target cells: $H-2^d$ P815 mastocytoma cells (ATCC No. TIB-64) and the $H-2^b$ thymoma EL4 (ATCC No. TIB-39) as a negative control.

We grew P815 and EL4 cells in RP10 medium (standard RPMI 1640 (Gibco/BRL, Grand Island, N.Y.) supplemented with 10% FBS (Hyclone) as well as 4 mM glutamine (Gibco/BRL), 100 I.U./ml penicillin+100 MCG/ml streptomycin (Gibco/BRL), 50 μM β-mercaptoethanol (Gibco/BRL) and 10 mM HEPES buffer (Gibco/BRL). On the day of assay, 1-2×10$^6$ target cells were harvested and resuspended at 2.5-5×10$^6$ cells/ml in RP10 medium. We added 50-100 μl of 5 mCi/ml $^{51}$Cr-sodium chromate (NEN, Boston, Mass.) directly to the cells and incubated them for 1 hour at 37° C., then washed them twice with 12 ml of PBS and resuspended them in 2 ml of RP10 medium. After counting the cells on a hemacytometer, the target cells were diluted to 0.5-1×10$^5$ cells/ml and 100 μl (0.5-1×10$^4$ cells) were mixed with effector cells at various effector:target ratios. After a 4-hour co-incubation of effector cells and the labeled target cells at 37° C., half of the supernatant from each well was collected and counted in a gamma counter for 1 min/sample. The percentage of specific $^{51}$Cr release was calculated from the formula 100×(X−Y)/(Z−Y), where X is $^{51}$Cr release in the presence of effector cells, Y is the spontaneous release in the absence of effectors, and Z is the total $^{51}$Cr release from target cells incubated with 0.5% Triton X-100. Data were plotted as the % specific lysis versus the effector-to-target ratio in each well.

CTLs re-stimulated in the presence of rmIL-2 exhibited the highest lytic activity on the P815 target cells, achieving >70% specific lysis at an effector-to-target ratio of 33:1. The next most active CTLs were those re-stimulated in the presence of IL-21 rhIL-15 (62% specific lysis), followed by CTL cultured with rhIL-15 (~50% lysis), CTL cultured with IL-21 alone (30% lysis), and CTL re-stimulated with rat conA supernatant (~10% lysis). None of the CTL lysed the H-$2^b$ EL4 cells (all CTL lysed fewer than 2% of the EL4 targets, even at the highest effector-to-target ratio of 33:1). This pattern of cytokine enhancement of cytolysis (IL-2>IL-21+IL-15>IL-15>IL-21>conA SN) held true in 2 replicate experiments. These data demonstrate that IL-21, particularly in combination with IL-15, can enhance CTL effector function.

Example 9

IL-21 Modifies the Response of OT-I T Cells to OVA Peptide as Presented by Murine Dendritic Cells A. Isolation and Labeling of OT-I T Cells Mice bearing a transgenic T cell receptor specific for OVA257-264 in H-$2K^b$ are available (OT-I transgenics, Jackson Laboratories). Cells from lymph nodes from these animals were adherence depleted and the CD8 T cells (OT-I T cells) were enriched by negative selection using CD8 Cellect columns (Cedarlane Laboratories, Hornby, Ontario, Canada). Purity of CD8 T cells was assessed by flow cytometry and was typically 90-95% with <1% CD4 T cells.

OT-I T cells were labeled with carboxyfluorescein diacetate succinimidyl ester (CFSE; Molecular Probes, Eugene, Oreg.) by placing them in growth media comprising RPMI-1640 medium supplemented with 10% FCS (JRH, Lenexa Kans.; Hyclone, Logan Utah), 2 mM glutamine (Gibco BRL), 50 U/ml penicillin (Gibco BRL), 50 µg/ml streptomycin (Gibco BRL, Grand Island, N.Y.) and 50 µM 2-mercaptoethanol (Sigma, St Louis, Mo.) containing 5 µM CFSE for 5 min at room temperature. The cells were then washed three times, each time by resuspending in PBS containing 5% FBS, centrifuging 5 min at 300 g, 20° C., and removing the supernatant. Cells were resuspended in growth media prior to use.

B. Preparation of Murine Dendritic Cells

Bone marrow derived dendritic cells (DCs) from mouse bone marrow were cultured in growth media the presence of GM-CSF using well-known methods (e.g., Inaba, K. et al., *J. Exp. Med.* 176:1693-1702, 1992). After six days in culture they were stimulated with 1 µg/ml LPS (Sigma, St Louis, Mo.) overnight and then washed in growth media prior to use.

C. In Vitro Stimulation of T Cells

DCs prepared as above were pulsed with 10 nm OVA257-264 peptide (SEQ ID NO:9) for 2 hours. The pulsed DCs are washed in growth media to remove any unbound peptide and then cultured with purified OT-I T cells prepared as described above in the presence of either media alone or 20 ng/ml mouse rIL-2 (R&D Systems, Minneapolis, Minn.) or 50 ng/ml murine IL-21 (U.S. Pat. No. 6,307,024). After either 48 or 72 hours of incubation the cells were harvested and analyzed by flow cytometry for levels of CFSE fluorescence and Annexin V binding (Pharmingen, San Diego, Calif.) per manufacturers instruction.

Results showed that when OT-I T cells are presented specific antigen on DC's they undergo 3-5 rounds of cell division by day 2 and 5-7 rounds of cell division by day 3 as evidenced with CFSE labeling. In the presence of IL-2 their proliferation is increased such that by day 2 they have gone 5-6 rounds and by day 3, 7-9 rounds. When the T cells are treated with IL-2 they undergoing apoptosis at day 3 as demonstrated by Annexin V binding. In contrast to IL-2, IL-21 induces increased T cell proliferation and prevents Annexin V labeling up to day 3. IL-21 continues to enhance proliferation and prevent apoptosis even in the presence of added IL-2.

IL-21 both enhances proliferation and reduces apoptosis of the murine CTL cells. This activity implies a positive immunostimulatory role for IL-21 in clinical settings, such as cancer or viral disease, where CTL's can play a role.

Example 10

IL-21 Promotes IL-2 Stimulated NK-Cell Expansion in PBMNC Cultures in the Presence of IL-4

IL-4 inhibits the expansion of NK-cells stimulated with IL-2. In two experiments human peripheral blood mononuclear cells (PBMNCs) were seeded at 200,000 cells/well in alpha-MEM+ 10% autologous serum with 10 ng/ml IL-2 (R&D Systems, Minneapolis, Minn.) with or without 0.5 ng/ml IL-4 (R&D Systems, Minneapolis, Minn.), and with or without 10 ng/ml IL-21 (U.S. Pat. No. 6,307,024) and grown for 8 days. The number of viable cells per well was determined using standard methods and the cells analyzed by flow cytometry for expression of CD3, CD16, and CD56. NK-cells were defined as the CD56 positive CD3 negative population.

The cultures from the two donors cultured with IL-2 alone contained about 151,000 and 326,000 NK-cells respectively on day 8. The cultures from the two donors cultured with IL-2 and IL-21 contained about 446,000 and 588,000 NK-cells respectively. The cultures from the two donors cultured with IL-2 and IL-4 contained about 26,000 and 29,000 NK-cells on day 8. However, cultures from the two donors cultured with IL-2, IL-4 and IL-21 contained about 229,000 and 361,000 NK-cells representing an 8.8 and 12.5 fold increase in NK-cell yield over the culture with IL-2 and IL-4 only.

These results demonstrate that IL-21 promotes NK-cell expansion, and that IL-21 can largely overcome the inhibitory effects of IL-4 on NK-cell growth. In some diseases IL-4 expression can play a role in the pathology. For example mice bearing the B16F10 melanoma generate a large population of IL-4 producing CD4+ T-cells which appear to limit the host anti-tumor response. Furthermore, STAT 6 (required for IL-4 signaling) gene deficient mice exhibit an enhanced ability to reject tumors. The ability of IL-21 to antagonize the action of IL-4, and induce the expression of Interferon-γ (described herein), in addition to the in vivo anti-tumor activity and data described herein, suggest that IL-21 can be useful in treating malignancies, infections or autoimmune disease where there is a Th2 response limiting the hosts ability to control the disease.

Example 11

IL-21 Stimulates Outgrowth of NK and NKT from Peripheral Blood Lymphocyte Cultures that Contain IL-2 or IL-15

Peripheral blood lymphocytes from 3 healthy human donors were prepared by the standard Ficoll centrifugation method. Lymphocytes were then cultured at a starting concentration of 200,000/ml in alpha MEM with 10% donor serum, 50 µM BME (Sigma), 2 ng/ml flt3L (R&D Systems), and 0, 0.5, 10, or 50 ng/ml of IL-2 (R&D Systems) or IL-15 (R&D Systems)+/-0, 5, or 50 ng/ml IL-21 (U.S. Pat. No. 6,307,024). After 12 days of culture cells were harvested, counted, and analyzed by flow cytometry for CD3, CD56, and CD8. NK cells were defined as CD56+/CD3- and NKT cells were defined as CD56+/CD3+.

The "fold increase" in cell number (defined as final cell number/starting cell number) was widely variable between the three donors, but the trends were fairly consistent. In general, the results at 10 ng/ml of IL-2 or IL-15 were similar to the results obtained with 50 ng/ml of IL-2 or IL-15, and the results at 5 ng/ml IL-21 were similar to those obtained with 50 ng/ml IL-21. With no IL-2 or IL-15 present, the fold increase in total cells was 0.33, 0.23, and 0.19 among the three donors. When 5 ng/ml IL-21 was included in the culture, the fold increases were 0.47, 0.31, and 0.35. At a low concentration of 0.5 ng/ml IL-2, we saw total cell fold increases of 2.2, 1.1, and 1.0 among the three donors. When 5 ng/ml IL-21 was included, we saw total cells increase by 5.5, 2.3, 3.1. We saw fold increases in NK numbers without IL-21 of 16, 4.2, and 3.5. When IL-21 was present (at 5 ng/ml) these increases were 24, 15, and 21 respectively. NKT's were also positively effected under these conditions. NKT fold increases were 4.4, 5.7, and 1.8 without IL-21, and 10, 9, and 15 with 5 ng/ml IL-21.

These results are mirrored with IL-15. At 0.5 ng/ml IL-15, total cell fold increases of 0.98, 0.43, and 0.88 were seen among the three donors. When 5 ng/ml IL-21 was included, we saw total cells increase by 1.4, 0.9, 1.7 fold. Fold increases of NK numbers of 8.0, 0.85, and 3.7 were seen without IL-21. When 5 ng/ml IL-21 was present, these fold increases were 13, 5.5, and 11. NKT fold increases at 0.5 ng/ml IL-15 were 3.3, 2.3, and 1.6 for the three donors, but they were 3.9, 5.2, and 4.7 when 5 ng/ml IL-21 was included.

At higher concentrations of IL-2 the fold increases were overall higher, but the effect of IL-21 was in general decreased, although still positive. At 10 ng/ml IL-2 we saw total cell fold increases of 18, 2.5, and 2.8 among the three donors. When 5 ng/ml IL-21 was included, we saw total cells increase by 21, 3.6, 9.8 fold. We saw fold increases in NK numbers of 114, 13, and 13 without IL-21. When IL-21 was also present (at 5 ng/ml) these increases were 100, 19, and 56 respectively. NKT's were also positively effected under these conditions. NKT fold increases were 33, 15, and 12 without IL-21, and 52, 20, and 38 with 5 ng/ml IL-21.

At 10 ng/ml IL-15, we saw total cell fold increases of 18, 0.8, and 1.7 among the three donors. When 5 ng/ml IL-21 was included, we saw total cells increase by 23, 1.4, 6.9 fold. We saw fold increases of NK numbers of 128, 0.58, and 2.0 without IL-21. When 5 ng/ml IL-21 was present, these fold increases were 107, 1.1, and 9.4. NKT fold increases at 10 ng/ml IL-15 were 60, 6.5, and 5.7 for the three donors, but they were 66, 12, and 33 when 5 ng/ml IL-21 was included.

IL-21's effects in these cultures were dependent on the presence of at least low dose IL-2 or IL-15. Without those cytokines, the effect of IL-21 was minimal. When IL-2 or IL-15 is present, especially at the lower, perhaps physiological, concentrations, IL-21's effect is the most profound. The lack of effect of IL-21 alone, coupled with its ability to synergize with low concentrations of other cytokines may allow it to act therapeutically at sites of infection or malignancy without causing systemic toxicity.

Example 12

IL-21 Inhibits the Production of IL-13 in NK-Cell Cultures

IL-13 shares receptor subunits and many of the biological activities of IL-4, but unlike IL-4, IL-13 is produced by NK-cells. Since NK-cells also produce IFN-gamma, and these two cytokines have in large part opposing activities, experiments were conducted to examine the effects of IL-21 on IL-13 and IFN-gamma expression in PBMNC and NK-cell cultures.

Negatively selected human peripheral blood NK-cells were seeded at about $3.75 \times 10^5$ cells/ml and stimulated 2 days with 10 ng/ml IL-2, IL-4 (R&D Systems) or IL-21 (U.S. Pat. No. 6,307,024) or without any cytokine in alpha-MEM+10% autologous serum. After two days in culture IL-2 was added to all wells to 10 ng/ml, and the cell were cultured for an additional 3 days, then the supernatants were collected and analyzed by ELISA for IL-13 and IFN-γ. NK-cells grown for two days without any cytokine produced about 2130 pg/ml IFN-γ and 175 pg/ml IL-13. Cells stimulated with IL-21 produced abut 10,300 pg/ml IFN-γ and 90 pg/ml IL-13. Cells stimulated with IL-2 produced 12,700 pg/ml IFN-γ and 1000 pg/ml IL-13. Cells stimulated with IL-4 produced no detectable IFN-γ nor IL-13.

Of note, cells stimulated for the first two days with IL-21 produced 5 times more IFN-γ, but only one half the IL-13 of unstimulated cells. When compared to cell stimulated with IL-2 for the first two days of culture cells stimulated with IL-21 produced 80% as much IFN-γ, but only 9% as much IL-13. Thus IL-21 selectively promotes the expression of IFN-γ and depresses IL-13 expression.

Example 13

IL-21 Synergizes with IL-2 to Promote IFN-γ Production in Mouse Splenic NK Cells C57BL/6 mouse splenic NK cells were prepared by water lysing a cell suspension from the spleens, then utilizing the Stem Cell Technologies murine NK negative enrichment magnetic cell sorting protocol. The cells prepared using this method were 65% Pan NK positive based on flow analysis using the DX5 Pan NK antibody from PharMingen.

The negatively enriched murine NK cells were cultured for 8 days at 500,000 cells/ml in RPMI 1640 with 10% heat inactivated fetal bovine serum and 2 mM L-glutamine, 50 μM BME, and PSN antibiotic with 20 ng/ml mIL-2 (R&D Systems) or 10 ng/ml mIL-21 or both. The cell supernatants were harvested and cells were counted at the end of the culture period. Cell supernatants were assayed for mIFN-γ using a commercially available ELISA kit from PharMingen.

Cell numbers at the end of the eight day period were about 1,300,000 for the IL-2 containing culture, 220,000 for the IL-2/IL-21 culture, and 10,000 for the IL-21 culture. The mIFN-γ levels were 2.2 ng/ml, 30 ng/ml, and 0.28 ng/ml respectively. When expressed as pg/500,000 cells, the results are 238, 14,000, and 12,000. IL-21 enhances IFN-γ expression in these cultures, which when combined with the cell survival/proliferation effects of IL-2, results in high levels of IFN-γ being secreted into the medium. IFN-γ is an important initiator of the immune response, and is considered a TH1 biased cytokine. This data supports that IL-21 plays a role in the antiviral activity of the immune system, and hence can be used as a therapeutic in anti-viral and other applications.

Example 14

LCMV Models

LCMV models are in vitro models to test a compound's effect on cells infected with a member of the Flaviviridae family, to which HCV is a member. These models are used to evaluate the effect IL-21 has on CTLs and the effect IL-21 has on viral load. There are two models that are used: LCMV Armstrong (acute) infection and LCMV Clone 13 (chronic) infection. (See, e.g., Wherry et al., *J. Virol.* 77:4911-4927, 2003; Blattman et al., *Nature Med.* 9(5):540-547, 2003; Hoffman et al., *J. Immunol.* 170:1339-1353, 2003.) There are three stages of CD8 T cell development in response to virus: 1) expansion, 2) contraction, and 3) memory (acute model).

IL-21 is injected during each stage for both acute and chronic models. In the chronic model, IL-21 is injected 60 days after infection to assess the effect of IL-21. For both acute and chronic models, IL-21 is injected, and the following parameters are examined: tetramer staining by flow to count the number of LCMV-specific CD8+ T cells; the ability of tetramer+ cells to produce cytokines when stimulated with their cognate LCMV antigen; and the ability of LCMV-specific CD8+ T cells to proliferate in response to their cognate LCMV antigen. LCMV-specific T cells are phenotyped by flow cytometry to assess the cells activation and differentiation state. Also, the ability of LCMV-specific CTL to lyse target cells bearing their cognate LCMV antigen is examined. The number and function of LCMV-specific CD4+ T cells is accessed, except for in the cytolysis assay.

Improvement in the quality and quantity of LCMV specific CD8+ T cells after IL-21 administration is determined. Specifically, results in increased cytokine production, especially IFN-γ increased percentages of tetramer+ cells that proliferate and an increase in the cytolytic activity are shown. The phenotype of CD8+ T cells from IL-21 treated mice reflects differentiation to an effector cell, that is, loss of CD27 expression and loss of CCR7 expression as well as increased perforin and granzyme B expression. Also, a reduction in viral load after treatment with IL-21 is shown. For IL-21 treated mice a 20% increase in the percentage of tetramer positive T cells that proliferate, make cytokine, or display a mature phenotype relative to untreated mice, is considered significant. A 20% increase in cytolytic activity is considered significant.

IL-21 injection leading to a reduction in viral load is due to more effective control of viral infection especially in the chronic model where untreated the viral titers remain elevated for an extended period of time. A 5 fold reduction in viral titer relative to untreated mice is considered significant.

Example 15

Ex Vivo Studies of Human CTL from HCV Patients

Blood obtained from chronically infected HCV patients and HCV-specific CTL is examined in vitro after culture with IL-21. The HCV-specific T cells are enumerated by staining with tetramers containing HCV peptides and soluble HLA Class I proteins. Using flow cytometry the ability of CD8+ HCV-specific T cells to proliferate and produce cytokines (especially interferon-γ and IL-2) in response to HCV antigens incubated in the presence or absence of IL21 is accessed. HCV-specific CTLs are phenotyped with respect to activation state and effector function (specifically for CD27 and CCR7 expression). Cytolytic activity for HLA-matched target cells bearing HCV peptides is also evaluated. (See, e.g., Wedemeyer et al., *J. Immol.* 169:3447-58, 2002; Gruener et al., *J. Virol.* 75:5550-58, 2001; Cramp et al., *Gastroenterology* 118: 346-55, 2000.)

In vitro culture of HCV-specific T cells with their cognate antigen with IL-21 is measured to demonstrate increased survival, proliferation, and cytokine production by the CTL, as compared to those cultured in media alone. Cytolytic activity of the HCV specific CTL is measured to demonstrate significant increases after culture in IL-21 relative to the same CTL cultured in media.

Example 16

Influenza Model of Acute Viral Infection

A. Preliminary Experiment to Test Antiviral Activity.

To determine the antiviral activity of IL-21 on Influenza virus and measure various immune parameters, focusing on cell-mediated and humoral immunity, an in vivo study using influenza infected c57Bl/6 mice was performed using the following protocol:

Animals: 6 weeks-old female BALB/c mice (Charles River) with 148 mice, 30 per group.

Groups:
(1) Absolute control (not infected) to run in parallel for antibody titer and histopathology (2 animals per group)
(2) Vehicle (i.p.) saline
(3) Amantadine (positive control) 10 mg/day during 5 days (per os) starting 2 hours before infection
(4) IL-21 treated (5 μg, i.p. starting 2 hours after infection)
(5) IL-21 (25 μg, i.p. starting 2 hours after infection)
(6) IL-21 (125 μg, i.p. starting 2 hours after infection)

Day 0—Except for the absolute controls, all animals infected with influenza virus
  For viral load (10 at LD50)
  For immunology workout (LD30)
Day 0-9—daily injections of IL-21 (i.p.)
  Body weight and general appearance recorded (3 times/week)
Day 3—sacrifice of 8 animals per group
  Viral load in right lung (TCID50)
  Histopathology in left lung
  Blood sample for antibody titration
Day 10—sacrifice of all surviving animals collecting blood samples for antibody titration, isolating lung lymphocytes (4 pools of 3) for direct CTL assay (in all 5 groups), and quantitative immunophenotyping for the following markers: CD3/CD4, CD3/CD8, CD3/CD8/CD11b, CD8/CD44/CD62L, CD3/DX5, GR-1/F480, and CD19.

Results demonstrated IL-21 treatment enhanced the virus specific cytolytic activity of pulmonary mononuclear cells. This enhanced CTL activity is hypothesized to be important for resolution of human viral disease. The treatment had no significant effect on day 4 viral load, day 10 antibody production or weight loss. The failure to alter day 4 viral load suggests that IL-21 treatment did not significantly enhance NK activity. Day 10 antibody production is an early time point of uncertain significance. The failure to alter weight loss suggests that IL-21 enhancement of CTL activity was inadequate to alter the course of the infection. This could be because the infection was simply too aggressive.

B. Secondary Experiment to Test for Antiviral Activity.

Study No 1:

1. $LD_{50}$ determination of a new stock of mouse-adapted influenza virus and analysis of the capacity to induce immune responses in infected C57Bl/6 mice. First, two new stocks of human influenza virus are produced and titrated. Second, the last passage of mouse-adapted virus is passaged in embryonated eggs. Also, a non-adapted virus stock (ATCC frozen stock) passaged in embryonated eggs. Third, an allantoic fluid control stock is prepared in embryonated eggs inoculated with PBS. Both stocks are titrated by HAU (using 0.5% rooster erythrocytes) and $TCID_{50}$ (using MDCK cells). The virus stocks and allantoic fluid control are frozen at −80° C.

2. Determination of the $LD_{50}$ for mouse-adapted virus stocks in C57Bl/6 mice is made using 6 Female C57Bl/6 mice (8 weeks-old) (Charles River). The mice are given an intranasal inoculation (20 μl) with a micropipette of anaesthetized animals (Ketamine/xylazine, i.p.), and then given 6 doses of each virus stock (1/10 dilution)+PBS control. There are 8 animals per dose. The numbers of animals are recorded daily, and the body weight measured every other day.

On day 14 post-infection, the number of animals that survived the virus challenge and their body weight are recorded, and the $LD_{30}$ for both virus stocks for C57Bl/6 mice is calculated.

3. Immune response induced by mouse-adapted influenza virus in C57BL/6 mice is analyzed.

CTL-mediated cytotoxicity is assayed using effector cells (mononuclear cells from the lungs), 10 days post infection in mice given 1 $LD_{30}$ of virus stock. The target cells are influenza-infected EL-4 (H-$2^b$) tumor cell line ATCC #TIB39 (Brit. J. Cancer 4: 372, 1950) Assays are done in quadruplicates at different E:T ratios starting from 50:1. In addition to compare susceptibility of target cells infected with non-adapted and mouse-adapted A/PR/8/34 influenza virus, uninfected target cells and EL-4 cells infected with B-Lee/40 influenza virus are used for specificity control. Three experiments are done to compare CTL responses in mice infected with the virus stocks.

Immunophenotyping: Preliminary immunophenotyping experiments are done on 3 pools of mononuclear cells from the lungs harvested on Day 10 post-infection from 3 mice infected with 1 $LD_{30}$ of mouse-adapted virus. Lung cell populations of interest are also be determined in normal C57BL/6 mice using pooled cells from 8 mice for each determination. These studies will use 44 animals.

Study No. 2:

To determine infecting doses at which clinical signs of illness (loss of weight) are not too severe while still inducing a detectable but suboptimal lung CTL, response a dose response study starting with the $LD_{30}$ of mouse-adapted virus is tested. The experiment uses 40 female C57Bl/6 mice (8 weeks-old) (Charles River), and the animals are anaesthetized. There are 4 groups of 2 animals for 1 $LD_{30}$ and of 4 animals per dose for lower doses. The doses are 1 LD30, 1/10 dilution, 1/100 dilution of virus.

The number of animals are recorded daily, and body weight is recorded every other day. Day 10 post-infection: Record the number of animals that survived the virus challenge and their body weight. On day 10, the animals are sacrificed and evaluated for CTL induction in 4 pools per dose (2 or 4 animals per pool), using uninfected, A/PR/8/34 and B/Lee/40-infected EL-4 as targets and 7 different E:T ratio (50/1, 25/1, 12/1, 6/1; 3/1, 1.5/1; and 0.75/1).

Study No. 3

Efficacy study of IL-21 in C57Bl/6 mice infected with mouse-adapted virus is done using 8 weeks-old female C57Bl/6 mice (Charles River). The groups have 36 animals per group.

Group 1: Vehicle (i.p.)
Group 2: Positive control: Anti-influenza neutralizing antibody (goat anti-influenza A/USSR (H1N1) (Chemicon International, Temecula, Calif.); 40 µg/mouse at 2 h and 4 h post infection (10 µl intranasal)
Group 3: ZG-01 (5 µg, i.p.)
Group 4: ZG-01 (25 µg, i.p.)
Group 5: ZG-01 (125 µg, i.p.)

TABLE 11

| Treatment Groups | Sacrificed at Day 10 | |
|---|---|---|
| | Immunology | RNA + IHC + H&E |
| Group 1 (28 mice) Vehicle | 24 animals (6 mice/pool) | 4 animals |
| Group 2 (28 mice) +ve control (Neutralizing Ab) | 24 animals (6 mice/pool) | 4 animals |

TABLE 11-continued

| Treatment Groups | Sacrificed at Day 10 | |
|---|---|---|
| | Immunology | RNA + IHC + H&E |
| Group 3 (28 mice) IL-21 (5 µg) | 24 animals (6 mice/pool) | 4 animals |
| Group 4 (28 mice) IL-21 (25 µg) | 24 animals (6 mice/pool) | 4 animals |
| Group 5 (28 mice) IL-21 (125 µg) | 24 animals (6 mice/pool) | 4 animals |
| Total (140 animals) | 120 | 20 |

Following-life observations and immunological workouts are prepared:

Day 0—all animals infected with Influenza virus (dose determined in experiment 2)

Day 0-9—daily injections of IL-21 (i.p.)

Body weight and general appearance recorded every other day

Day 10—sacrifice of surviving animals (24 animals will be used for complete immune evaluation; 4 for DNA isolation and H&E staining)

Isolation of lung lymphocytes (4 pools of 6) for direct CTL assay in the lungs (in all 5 groups) using EL-4 as targets and different E:T ratio (based on best results from experiments 1 and 2).

Tetramer staining: The number of CD8+ T cells binding MHC Class I tetramers containing influenza A nucleoprotein (NP) epitope are assessed using complexes of MHC class I with viral peptides: FLU-NP$_{366-374}$/D$^b$ (ASNENMETM), (LMCV peptide/D$^b$).

Quantitative immunophenotyping of the following: CD8, tetramer, intracellular IFNγ, NK1.1, CD8, tetramer, CD62L, CD44, CD3(+ or −), NK1.1(+), intracellular IFNγ, CD4, CD8, NK1.1, DX5, CD3 (+ or −), NK1.1, DX5, tetramer, Single colour samples for cytometer adjustment.

Survival/Re-Challenge Study

TABLE 12

| Treatment Groups | Re-challenged with 1LD$_{30}$ | Re-challenged with 5LD$_{50}$ |
|---|---|---|
| Group 6 (32 mice) Vehicle | Group 6A 12 animals | Group 6B 20 animals |
| Group 7 (32 mice) IL-21 (125 µg) | Group 7A 12 animals | Group 7A 20 animals |
| Total (64 animals) | 24 animals | 40 animals |

Day 30: Survival study (12 animals per group) with mice are treated for 9 days with different doses of IL-21 or with positive anti-influenza antibody control. Body weight and antibody production in individual serum samples (Total, IgG1, IgG2a, IgG2b) are measured.

Re-Challenge Study:

2 groups of 32 animals are used in this study.

Day 0: Both groups will be infected with A/PR virus (1LD30).

Group 6 will not be treated.

Group 7 will be treated for 9 days with 125 µg of IL-21.

Day 30: Survival study

Body weight and antibody production in individual serum samples (Total, IgG1, IgG2a, IgG2b) are measured.

Day 60: Re-challenge study

Survivors in each group will be divided into 2 subgroups

Group 6A and 7A will be re-challenge with A/PR virus (1 LD30)

Group 6B and 7B will be re-challenge with A/PR virus (1 LD30).

Both groups will be followed up and day of sacrifice will be determined. Body weight and antibody production in individual serum samples (Total, IgG1, IgG2a, IgG2b) are measured.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. A method of treating an infection comprising administering a therapeutically effective amount of a polypeptide that has at least 90% identity to an IL-21 polypeptide comprising residues 32 (Gln) to 162 (Ser) of SEQ ID NO:2 wherein the residue at position 44 is Asp, the residue at position 47 is Asp and the residue at position 135 is Glu, wherein the polypeptide binds an IL-21 receptor as shown in SEQ ID NO:6, wherein the infection is Influenza viruses.

2. The method according to claim 1, wherein the polypeptide has at least 95% identity to an IL-21 polypeptide comprising residues 32 (Gln) to 162 (Ser) of SEQ ID NO:2 wherein the residue at position 44 is Asp, the residue at position 47 is Asp and the residue at position 135 is Glu, wherein the polypeptide binds an IL-21 receptor as shown in SEQ ID NO:6.

3. The method according claim 1, wherein the polypeptide is an IL-21 polypeptide comprising residues 32 (Gln) to 162 (Ser) of SEQ ID NO:2.

4. The method according to claim 1, such that the level of viral infection is reduced.

5. The method according to claim 1, wherein a reduction in the level of viral infection is measured as reduction in viral load, increased viral-specific antibodies, or reduction in alanine aminotransferase level (ALT).

6. A method of treating an infection comprising administering a therapeutically effective amount of a fusion protein comprising a first polypeptide that has at least 90% identity to an IL-21 polypeptide comprising residues 32 (Gln) to 162 (Ser) of SEQ ID NO:2 wherein the residue at position 44 is Asp, the residue at position 47 is Asp and the residue at position 135 is Glu, wherein the polypeptide binds an IL-21 receptor as shown in SEQ ID NO:6, and a second polypeptide, wherein the infection is Influenza viruses.

* * * * *

UNITED STATES PATENT AND TRADEMARK OFFICE
CERTIFICATE OF CORRECTION

| | | |
|---|---|---|
| PATENT NO. | : 7,959,908 B2 | Page 1 of 1 |
| APPLICATION NO. | : 12/355650 | |
| DATED | : June 14, 2011 | |
| INVENTOR(S) | : Andrew Nelson et al. | |

It is certified that error appears in the above-identified patent and that said Letters Patent is hereby corrected as shown below:

On the Title Page:

Item (56) (Other Publications), line 45, delete "Repond" and insert -- Respond --, therefor.

Signed and Sealed this
Twentieth Day of December, 2011

David J. Kappos
*Director of the United States Patent and Trademark Office*